United States Patent
Erickson et al.

(10) Patent No.: US 8,585,202 B2
(45) Date of Patent: *Nov. 19, 2013

(54) CONTRAST SENSITIVITY TESTING AND/OR TRAINING USING CIRCULAR CONTRAST ZONES

(75) Inventors: Graham B. Erickson, Hillsboro, OR (US); Alan W. Reichow, Beaverton, OR (US); Herb Yoo, Beaverton, OR (US)

(73) Assignee: Nike, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/404,465

(22) Filed: Feb. 24, 2012

(65) Prior Publication Data

US 2012/0154744 A1     Jun. 21, 2012

Related U.S. Application Data

(63) Continuation of application No. 13/084,744, filed on Apr. 12, 2011, now Pat. No. 8,132,910, which is a continuation of application No. 12/500,353, filed on Jul. 9, 2009, now Pat. No. 7,942,525.

(51) Int. Cl.
    *A61B 3/00*     (2006.01)
    *A61B 3/02*     (2006.01)

(52) U.S. Cl.
    USPC ................ 351/203; 351/239; 351/246

(58) Field of Classification Search
    USPC ................................ 351/200–246
    See application file for complete search history.

(56) References Cited

U.S. PATENT DOCUMENTS

| | | | |
|---|---|---|---|
| 3,861,790 A | 1/1975 | Tamura | |
| 5,050,982 A | 9/1991 | Meissner | |
| 5,176,147 A * | 1/1993 | Bodis-Wollner | 600/558 |
| 5,478,239 A | 12/1995 | Fuerst et al. | |
| 5,825,460 A | 10/1998 | Kohayakawa | |
| 6,623,119 B2 | 9/2003 | Lehmeier | |
| 6,755,525 B2 | 6/2004 | Reichow et al. | |

(Continued)

FOREIGN PATENT DOCUMENTS

| DE | 102004053269 | 5/2006 |
|---|---|---|
| EP | 0838193 | 4/1998 |

(Continued)

OTHER PUBLICATIONS

Notice of Allowance for U.S. Appl. No. 13/084,744 dated Nov. 7, 2011.

(Continued)

*Primary Examiner* — Mohammed Hasan
(74) *Attorney, Agent, or Firm* — Shook, Hardy & Bacon L.L.P.

(57) ABSTRACT

The contrast sensitivity of an individual may be tested and/or trained using a plurality of circular contrast zones. The individual may select the circular contrast zone having a different degree of contrast than the other circular contrast zones. For example, the individual may select the circular contrast zone having the highest or lowest contrast of a displayed plurality of circular contrast zones. A plurality of circular contrast zones may be displayed with a spatial arrangement that facilitates inputting a selection of one of the plurality by the individual. A variety of input devices may be used to receive a selection from an individual. Both the accuracy and speed of an individual's contrast sensitivity may be tested and/or trained in accordance with the present invention.

14 Claims, 29 Drawing Sheets

(56) References Cited

U.S. PATENT DOCUMENTS

| | | | |
|---|---|---|---|
| 6,811,258 | B1 | 11/2004 | Grant |
| 6,893,127 | B2 | 5/2005 | Reichow et al. |
| 6,899,428 | B2 | 5/2005 | Mihashi |
| 7,073,208 | B2 | 7/2006 | Penque, Jr. et al. |
| 7,942,525 | B2 * | 5/2011 | Erickson et al. ............. 351/203 |
| 2007/0000007 | A1 | 1/2007 | MacDonald |
| 2009/0129205 | A1 | 5/2009 | Reichow |
| 2009/0130640 | A1 | 5/2009 | Hardy |
| 2009/0150919 | A1 | 6/2009 | Lee |

FOREIGN PATENT DOCUMENTS

| | | |
|---|---|---|
| WO | 2008128178 | 10/2008 |
| WO | 2008128187 | 10/2008 |
| WO | 2008128190 | 10/2008 |
| WO | 2008155544 | 12/2008 |

OTHER PUBLICATIONS

European Search Report dated Nov. 9, 2012 for EP 10797934.6.
Reichow, et al., "Introduction to Behavioral Optometry", Sports Vision, 1993, 75 pages, Optometric Extension Program Foundation, United States.
Ferreira, "An Overview of Research in Sports Vision: its History and an Optometric Perspective", The South African Optometrist, Dec. 2003, pp. 142-149, vol. 62, No. 4, Auckland Park, South Africa.
Coffey, et al., "Visual Performance Enhancement in Sports Optometry", Sports Vision 1995, pp. 158-177, Butterworth-Heinermann, United States.
Cardall, "Contact Lenses in Sport: a General Overview", Optician, Jan. 13, 2006, pp. 22-25, vol. 231, No. 6034, United States.
Rouse, et al., "A Comparison Study of Dynamic Visual Acuity Between Athletes and Nonathletes", Journal of the American Optometric Association, Dec. 1988, pp. 946-950, vol. 59, No. 12, United States.
Koenig, "Practicing Perception: Eyes Can Be Trained to be More Effective", USA Today Baseball Weekly, 1996, 3 pages, United States.
Coffey, et al., "Optometric Evaluation of the Elite Athlete," Problems in Optometry, Mar. 1990, pp. 32-59, vol. 2, No. 1, United States.
Reichow, et al., "A Comparison of Contrast Sensitivity in Elite Athletes Versus a Normal Population", American Journal of Optometry and Physiological Optics, Dec. 15, 1986, vol. 63, No. 82, United States.
Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.
Herdman, et al., "Computerized Dynamic Visual Acuity Test in the Assessment of Vestibular Deficits", The American Journal of Otology, 1998, pp. 790-796, vol. 19, No. 6, United States.
Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.
Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.
Internatinal Search Report and Written Opinion for PCT/US2010/041569 filed Jul. 9, 2010.

* cited by examiner

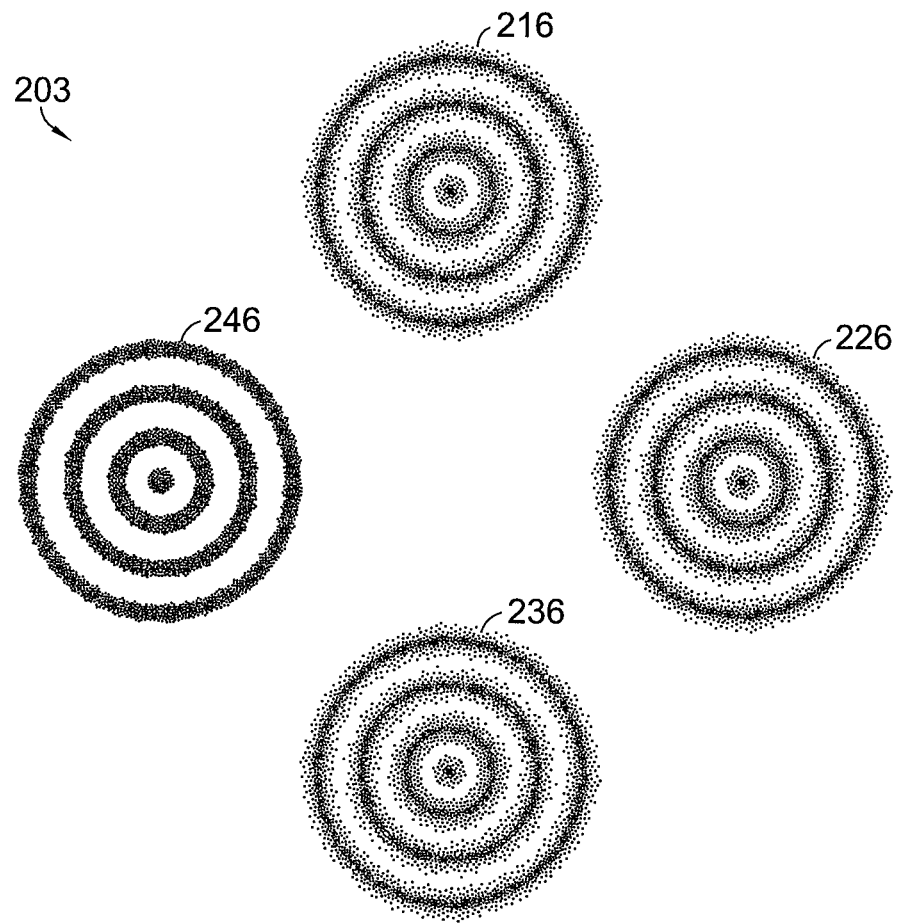
*FIG. 2D.*
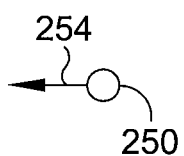

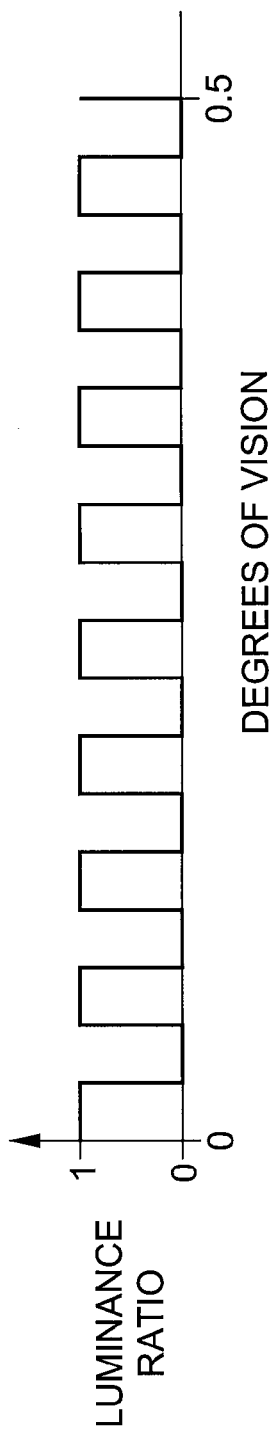
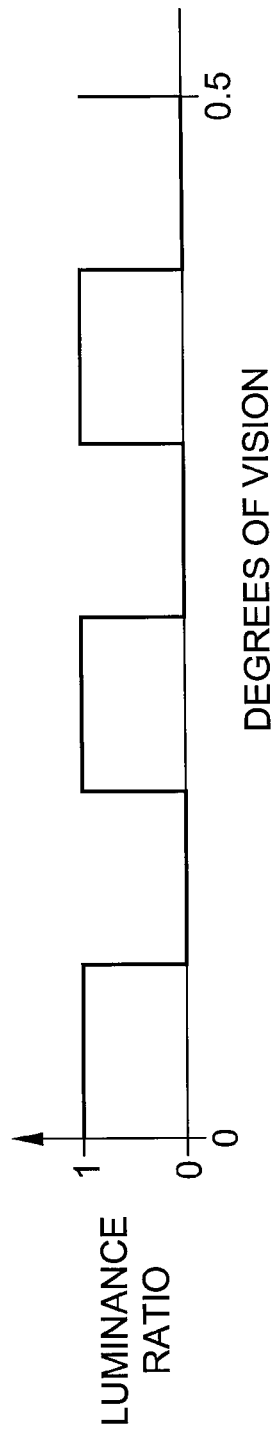

CONTRAST SENSITIVITY TESTING AND/OR TRAINING USING CIRCULAR CONTRAST ZONES

CROSS-REFERENCE TO RELATED APPLICATIONS

This application is a continuation of U.S. patent application Ser. No. 13/084,744, filed Apr. 12, 2011, Now U.S. Pat. No. 8,132,910 B2 entitled "Contrast Sensitivity Testing And/Or Training Using Circular Contrast Zones" which is a continuation of U.S. application Ser. No. 12/500,353, filed Jul. 9, 2009, now U.S. Pat. No. 7,942,525, granted May 17, 2011, entitled "Contrast Sensitivity Testing And/Or Training Using Circular Contrast Zones" which is herein incorporated by reference.

STATEMENT REGARDING FEDERALLY SPONSORED RESEARCH OR DEVELOPMENT

Not applicable.

TECHNICAL FIELD

The present invention relates to vision testing and/or training. More particularly, the present invention relates to testing and/or training the contrast sensitivity of a subject.

BACKGROUND OF THE INVENTION

Contrast sensitivity testing has been performed using a variety of systems and methods that test the ability of a subject to discern contrast patterns in visual indicia. Contrast sensitivity testing has been used to determine whether a subject has a deficiency in his or her contrast sensitivity.

BRIEF SUMMARY OF THE INVENTION

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

In accordance with the present invention contrast testing or training may utilize a plurality of circular contrast zones, with one of the plurality of circular contrast zones possessing a contrast pattern greater or lesser than the other circular contrast zones. Contrast sensitivity testing or training may proceed by asking a subject to select the contrast zone of the plurality having the highest or lowest contrast pattern. Each of the contrast zones presented at a given time may possess a total amount of pigmentation or coloration that is equivalent, with only the contrast of any given circular contrast zone varying. The plurality of circular contrast zones used in accordance with the present invention may be presented in a spatially distributed manner on a display device. Input(s) identifying one of the plurality of circular contrast zones may be received on an input device that enables a subject to provide one or more input corresponding to the spatial distribution of circular contrast zones on the display device, thereby enabling the subject to uniquely identify one or more circular contrast zone with an input. Appropriate input devices may include touch sensitive screens, joysticks, buttons, multitouch input devices, and the like.

BRIEF DESCRIPTION OF THE SEVERAL VIEWS OF THE DRAWING

The present invention is described in detail below with reference to the attached drawing figures, wherein:

FIGS. 2A-2D illustrate various pluralities of circular contrast zones and a joystick for use in accordance with the present invention;

FIGS. 14A-14B illustrate graphical depictions of the luminance patterns of square wave varying circular contrast zones as a function of visual angle.

DETAILED DESCRIPTION OF THE INVENTION

The subject matter of the present invention is described with specificity herein to meet statutory requirements. However, the description itself is not intended to limit the scope of this patent. Rather, the inventors have contemplated that the claimed subject matter might also be embodied in other ways to include different steps or combination of steps similarly to ones described in this document, in conjunction with other present or future technologies.

In contrast sensitivity testing, a contrast pattern is displayed to a subject to determine whether or not the subject can perceive the contrast pattern. One challenge in testing the contrast sensitivity of a subject arises if the subject possesses astigmatism, which may prevent the subject from perceiving contrast patterns when they are aligned with vision defects arising from that astigmatism. This difficulty may be overcome by using circular contrast zones which possess circular contrast patterns. The circular contrast pattern of such a circular contrast zone may extend in a 360° fashion so that it cannot be aligned with a given subject's visual defects resulting from astigmatism.

The spatial frequency of a circular contrast zone in accordance with the present invention may vary for different embodiments or for different testing/training iterations within the same embodiment. The spatial frequency of a circular contrast zone depends upon the size of the circular contrast zone, the distance of the subject from the display device displaying the circular contrast zone, and the number of contrast pattern cycles within the circular contrast zone. While a variety of contrast patterns may be used in accordance with the present invention, a symmetrical sinusoidal grating contrast pattern can present a relatively significant challenge to a subject. One example of sinusoidal grating contrast patterns are Gabor patches, which are sometimes used in contrast sensitivity testing. However, Gabor patches are not symmetrical and, therefore, the perception of the contrast pattern of a Gabor patch can be compromised by astigmatism. If a relatively small challenge to a subject is desired, a square wave contrast pattern may be used. Any type of contrast pattern may be utilized in a circular contrast zone in accordance with the present invention. If an irregular contrast pattern is used, the spatial frequency of the contrast pattern may vary along the radius of the circular contrast zone. If a regular contrast pattern is used, any spatial frequency may be utilized. The spatial frequency of the contrast pattern of a circular contrast zone may be expressed as a number of cycles per degree of vision of the subject. Spatial frequencies such as 18 cycles per degree and/or 6 cycles per degree may be used, for example. A wide range of contrasts may be tested across a wide range of spatial frequencies using circular contrast zones in accordance with the present invention.

Figure 13A:
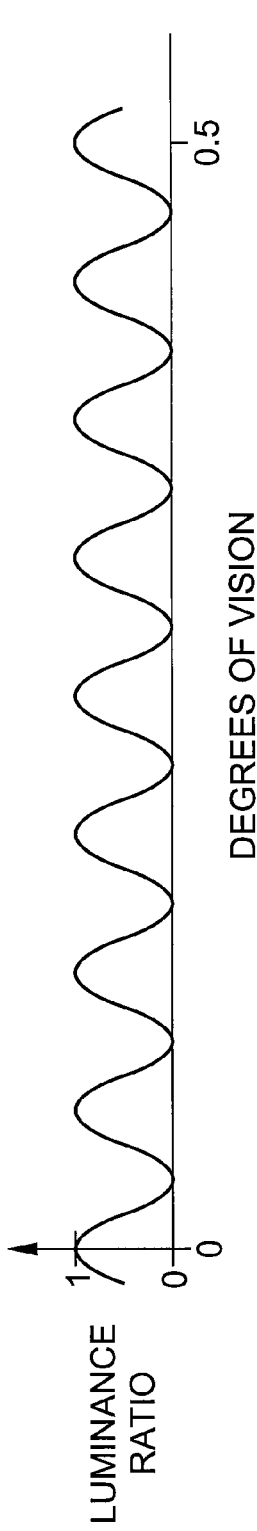
FIGS. 13A-13B illustrate graphical depictions of the luminance patterns of sinusoidally varying circular contrast zones as a function of visual angle.
Figure 13B:
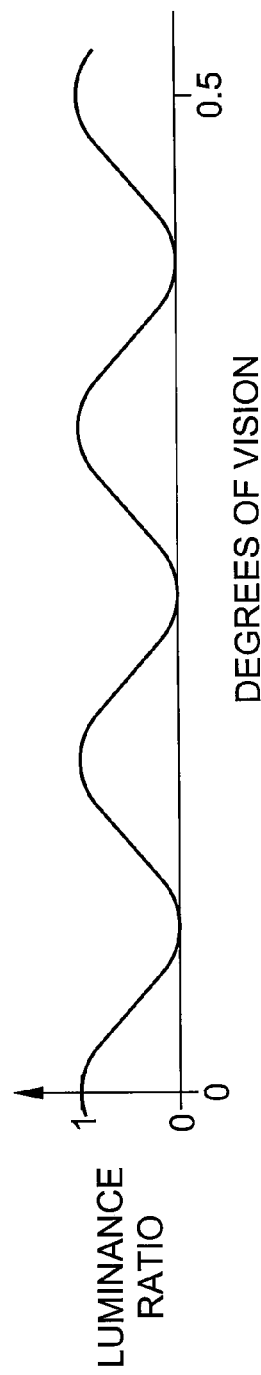

FIGS. 13A-13B and 14A-14B graphically illustrate exemplary luminance patterns that may be used in conjunction with circular contrast zones in accordance with the present invention as a function of visual angle. FIGS. 13A-13B and 14A-14B depict the luminance of a given contrast pattern as the luminance varies from the maximum luminance value within the circular contrast zone, denoted as "max," to the minimum luminance value within the circular contrast zone, denoted as "min," as the luminance varies across the angular field of view of a subject. While the maximum luminance and the minimum luminance depicted in FIGS. 13A-13B and 14A-14B may be the maximum luminance attainable by a display device and the minimum luminance attainable by a display device, respectively, the luminance of a given circular contrast zone need not vary over the full range of luminance possible for the display device utilized. FIGS. 13A-13B and 14A-14B depict the luminance of a circular contrast zone across one half of a degree of vision, although circular contrast zones may occupy more or less than this distance. FIGS. 13A-13B and 14A-14B depict the luminance across the diameter of exemplary circular contrast zones. FIG. 13A illustrates the sinusoidal variation of luminance with a frequency of 18 cycles per degree across the diameter of a circular contrast zone. FIG. 13B illustrates the sinusoidal variation of luminance with a frequency of 6 cycles per degree across the diameter of a circular contrast zone. FIG. 14A illustrates a square wave variation of luminance with a frequency of 18 cycles per degree across the diameter of a circular contrast zone. FIG. 14B illustrates a square wave variation of luminance with a frequency of 6 cycles per degree across the diameter of a circular contrast zone. Any cyclical or non-cyclical pattern may be used in conjunction with a circular contrast zone in accordance with the present invention beyond the patterns illustrated in FIGS. 13A-13B and 14A-14B. For example, a circular contrast zone may have a single portion with a luminance that differs from the rest of the circular contrast zone. By way of further example, a circular contrast zone may have a non-periodic variance in luminance.

Additionally, the present invention permits the use of a plurality of circular contrast zones simultaneously, from which a subject may select a single circular contrast zone. For example, a subject may be instructed to select the contrast zone having the highest or lowest contrast pattern. In this way, multiple test iterations may display a plurality of circular contrast zones with the test subject selecting one (such as the highest contrast pattern or the lowest contrast pattern), thereby accurately measuring the contrast sensitivity of a subject, rather than merely determining whether a subject may perceive a given degree of contrast, such as may be utilized for some screening purposes. The contrast of a circular contrast zone may be defined in a variety of ways. One useful measure of the contrast of a contrast zone is sometimes referred to as "modulation" or "Michelson contrast." The Michelson contrast, denoted M, may be calculated based on the maximum and minimum luminances of a contrast zone based on the equation: $M=(^L max - ^L min)/(^L max + ^L min)$. In some instances, a contrast zone may be uniform, such that $(^L max = ^L min)$, in which case $M=0$. Of course, other measures/definitions of contrast may be used. The contrast sensitivity testing in accordance with the present invention may utilize an input device that may receive inputs corresponding to a spatial distribution of the displayed circular contrast zones. In this fashion, a subject may easily and rapidly select an individual contrast zone that the subject believes to be the correct response to a given display of a plurality of contrast zones. An analysis of the time elapsed between the display of a plurality of contrast zones and the receipt of an input indicating the selection of one of the plurality of circular contrast zones may provide additional information regarding the contrast sensitivity abilities of a subject. A variety of input devices may be utilized in conjunction with contrast sensitivity testing in accordance with the present invention. Some of the examples described more particularly herein include joysticks, buttons, touch sensitive screens, and gesture recognition. However, any other type of input device may be utilized, such as voice recognition, foot pedals, balance boards, and the like. Further, systems and methods in accordance with the present invention may additionally or alternatively be used to train the contrast sensitivity of a subject.

Figure 1:
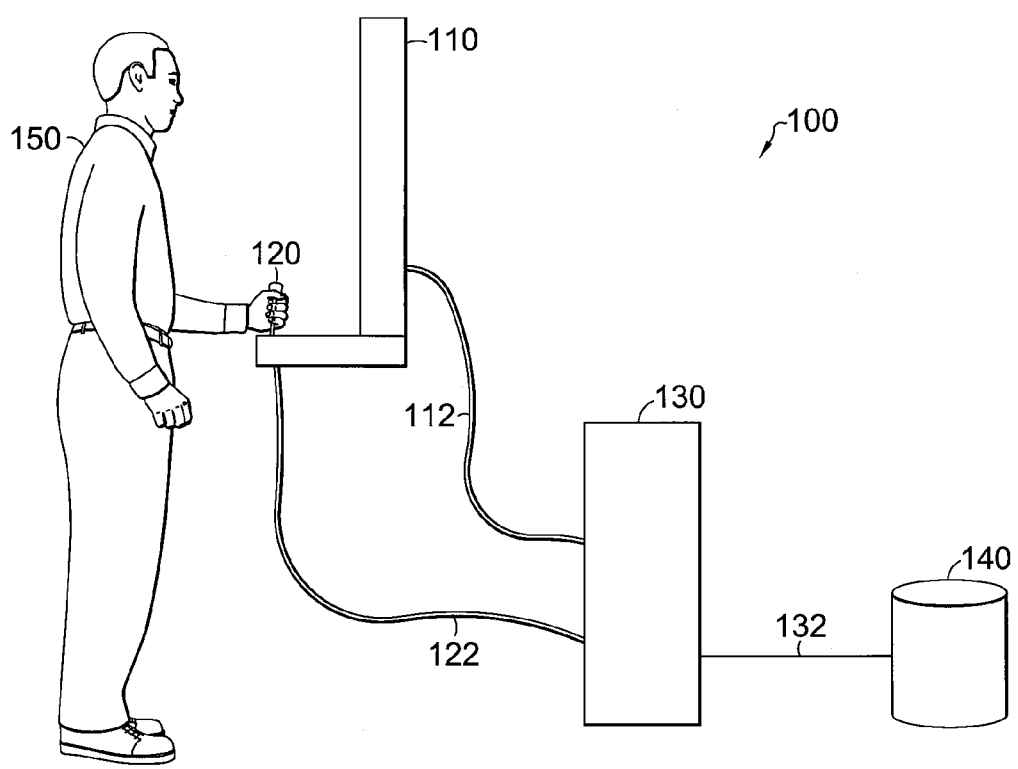
FIG. 1 illustrates a system for testing or training contrast sensitivity in accordance with the present invention.

Referring now to FIG. 1, a system 100 for contrast sensitivity testing or training is illustrated. Contrast sensitivity testing or training using system 100 may utilize display device 110 to present a plurality of circular contrast zones to subject 150. Subject 150 may select one of a plurality of displayed contrast zones using joystick 120. Testing unit 130 may operate in communication with display device 110 to cause display device 110 to display a plurality of circular contrast zones. While referred to as a "testing unit" or a "test unit" herein testing unit 130 may be used for testing and/or training contrast sensitivity. Testing unit 130 may communicate with display device 110 via cable 112, although any communication media and/or protocol may be used. In input from subject 150 registered using joystick 120 may be communicated to test unit 130 via cable 122. Various types of performance data, such as the contrast levels of a displayed plurality of circular contrast zones, the selections registered by subject 150, that respective times at which a plurality of circular contrast zones were displayed and an input was received, and other types of performance data may be communicated from testing unit 130 to storage device 140 via connection 132. Storage device 140 may be integral to testing unit 130, or may be a remote server, data base, storage drive, or other device. Similarly, storage device 140 may be distributed over a number of physical devices, and may comprise any number of devices or portions of devices used redundantly for backup purposes. Further, the various connections such as cable 112, cable 122, and connection 132 may utilize any type of connection operating on any standard or specialized communications particle, including wireless protocols.

Referring now to FIGS. 2A-2D, exemplary pluralities of circular contrast zones and corresponding inputs selecting a contrast zone using a joystick 250 are illustrated. The circular contrast zones illustrated in FIGS. 2A-2D, as well as FIGS. 4A-4D, 6A-6C, 8A-8O, and 10A-10D a plurality of dots are illustrated in each contrast zone, with the density of dots indicating the luminance, pigmentation, etc. at a particular position within a contrast zone, while dots, such as used in illustrations herein, may be used in circular contrast zones in connection with the present invention, variations in chromaticity, luminance, etc. may also be used.

Figure 2A:
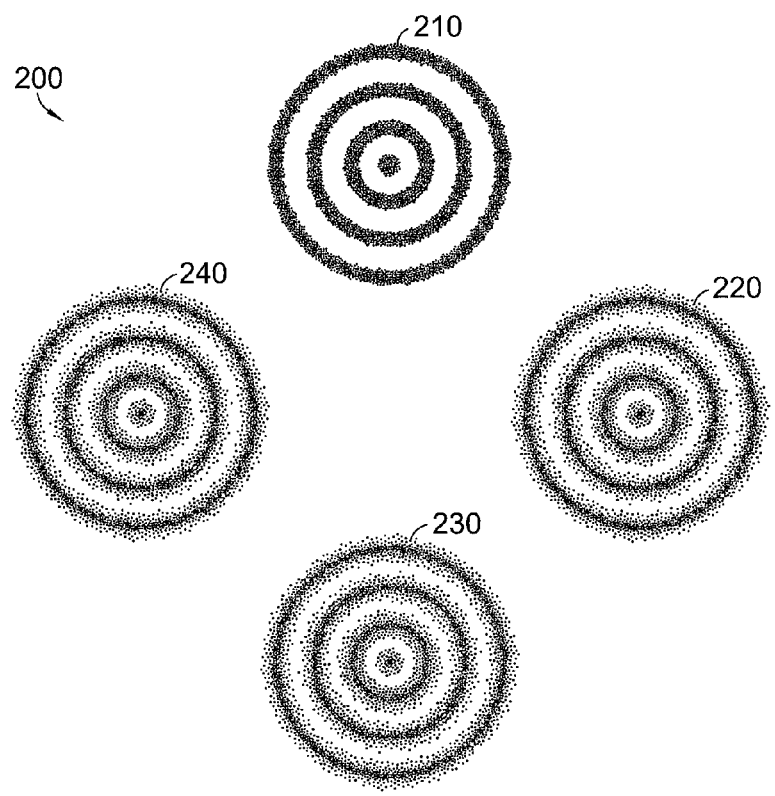
Figure 2A:
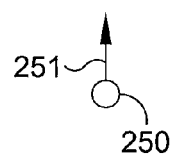

In FIG. 2A a plurality 200 of circular contrast zones may comprise a first circular contrast zone 210, a second circular contrast zone 220, a third circular contrast zone 230, and a fourth circular contrast zone 240. As illustrated in FIG. 2A, each of the plurality 200 of circular contrast zones possesses a spatial orientation relative to the other contrast zones. In this example, first circular contrast zone 210 may also be referred to as the top-contrast zone 210, second circular contrast zone 220 may also be referred to as the right contrast zone 220, third circular contrast zone 230 may also be referred to as the bottom contrast zone, and fourth circular contrast zone 240 may also be referred to as the left contrast zone. In the example illustrated in FIG. 2A, top-contrast zone 210 possesses a higher contrast pattern than the other circular zones in the plurality 200 of circular contrast zones. A subject (not illustrated) may register a selection of top-contrast zone 210 utilizing joystick 250 by engaging joystick 250 in an upward direction 251.

Figure 2B:
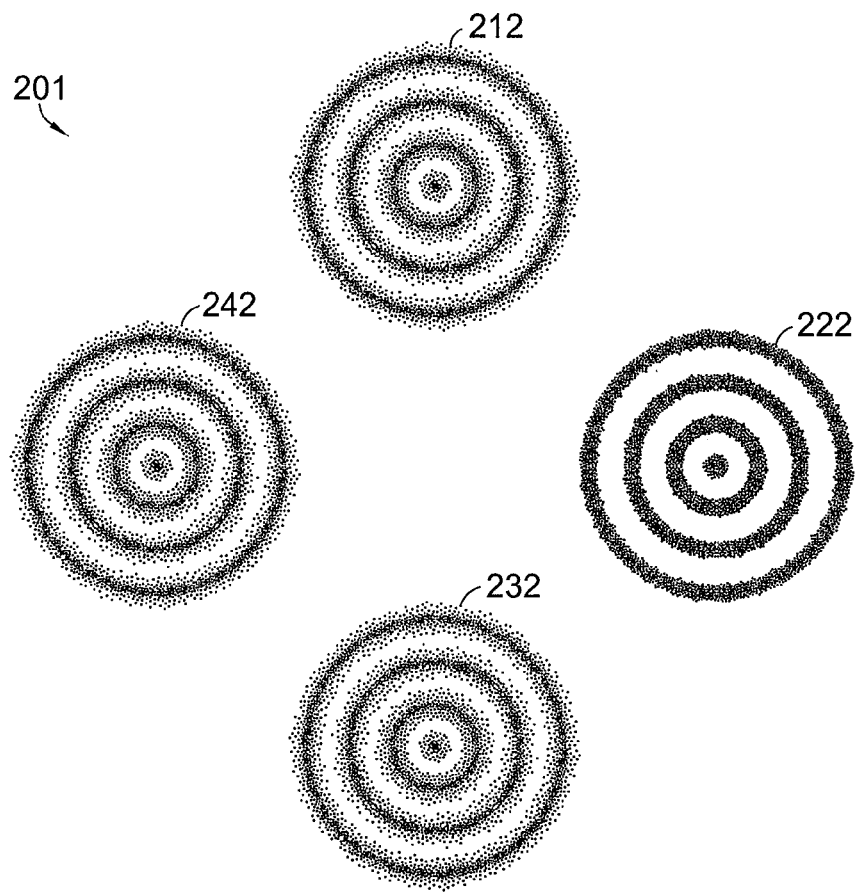
Figure 2B:
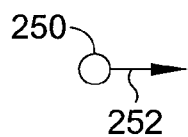

Referring now to FIG. 2B, a further plurality 201 of circular contrast zones is illustrated. Plurality 201 comprises top contrast zone 212, right contrast zone 222, bottom contrast zone 232, and left contrast zone 242. In the example of FIG. 2B, right contrast zone 222 possesses the highest contrast pattern of the plurality 201 of circular contrast zones. Accordingly, subject (not illustrated) may register an input selecting right contrast zone 222 using joystick 250 by engaging joystick 250 in a rightward direction 252.

Figure 2C:
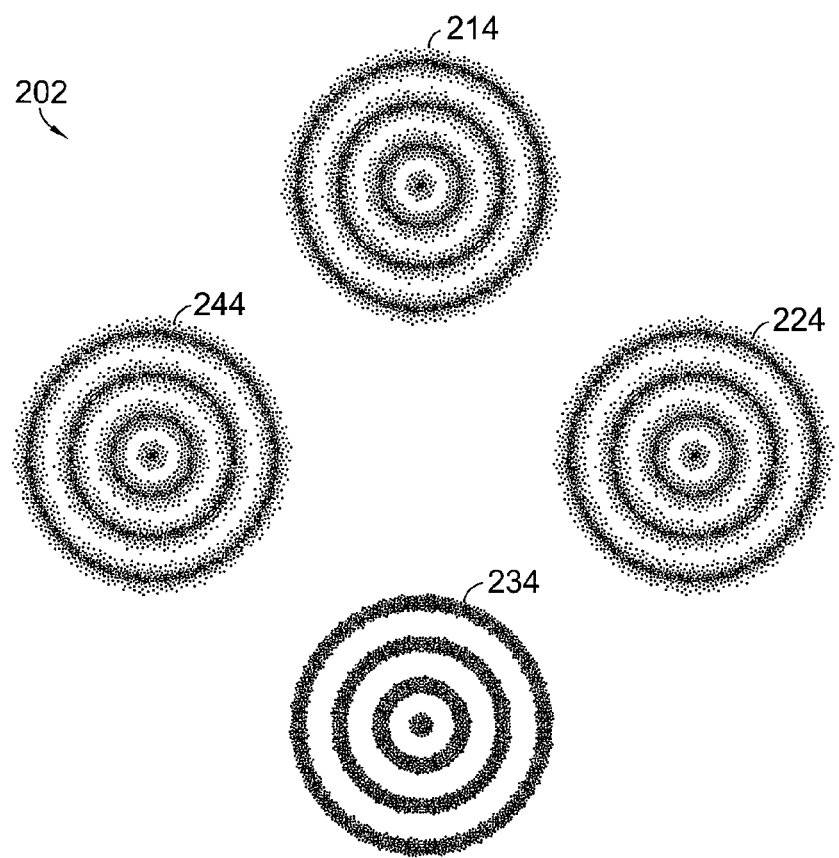
Figure 2C:
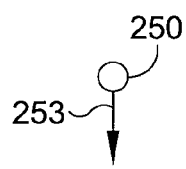

Referring now to FIG. 2C, a further plurality 202 of circular contrast zones is illustrated. Plurality 202 of circular contrast zones comprises top contrast zone 214, right circular contrast zone 224, bottom circular zone 234, and left circular zone 244. In the example illustrated in FIG. 2C, bottom contrast zone 234 possesses the highest contrast pattern of the plurality 202 of circular contrast zones. The subject (not illustrated) may indicate selection of bottom contrast zone 234 by depressing joystick 250 in a downward direction 253.

Referring now to FIG. 2D, a further plurality 203 of circular contrast zones is illustrated. Plurality 203 of circular contrast zones comprises top contrast zone 216, right contrast zone 226, bottom contrast zone 236, and left contrast zone 246. In the example illustrated in FIG. 2D, left contrast zone 246 possesses the higher contrast pattern than the other circular contrast zones of plurality 203 of circular contrast zones. Subject (not illustrated) may indicate the selection of left contrast zone 246 by engaging joystick 250 in a leftward direction 254.

Of course, it should be appreciated that the contrast patterns used in conjunction with contrast sensitivity testing in accordance with the present invention may vary significantly from those illustrated in FIGS. 2A-2D. Further, it should be appreciated that the order in which any given circular contrast zone of a plurality of circular contrast zones is the circular contrast zone to be selected by a subject may occur in any given order. Each of a plurality of circular contrast zones, such as those illustrated in FIGS. 2A-2D, may possess an equal amount of pigmentation, so that a subject cannot simply select a circular contrast zone as having the most or least total pigmentation without perceiving the contrast pattern within the contrast zone. However, such an approach is not necessary in accordance with the present invention. Moreover, while FIGS. 2A-2D illustrate the use of four circular contrast zones, with one as the top circular contrast zone, one as the right circular contrast zone, one as the bottom circular contrast zone, and one as the left circular contrast zone, more or fewer than four circular contrast zones may be utilized without departing from the scope of the present invention.

Figure 3:
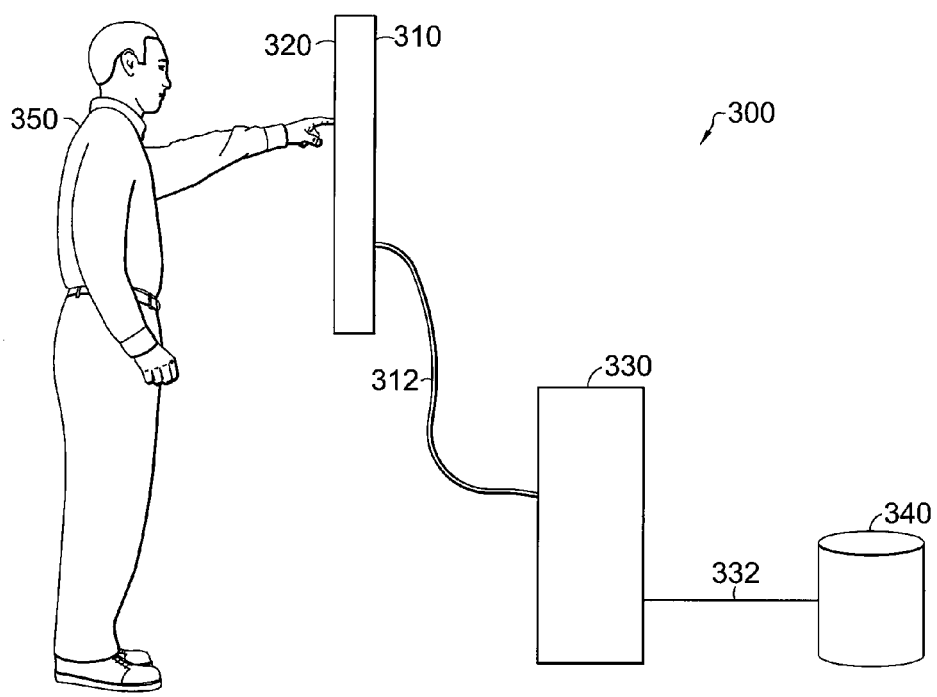
FIG. 3 illustrates a further system for testing or training contrast sensitivity in accordance with the present invention.

Referring now to FIG. 3, a further system 300 in accordance with the present invention for testing or training the contrast sensitivity of a subject 350 is illustrated. System 300 may utilize display device 310 having a touch sensitive screen 320. In this way, display device 310 may display a plurality of circular contrast zones to subject 350, and subject 350 may register a selection of one of the plurality of circular contrast zones by touching touch sensitive screen 320, for example at or near the selected circular contrast zone. Cable 312 may connect display device 310 to testing unit 330. While referred to as "testing unit" or "test unit" herein, testing unit 330 may be used to test and/or train contrast sensitivity. Testing unit 330 may operate to cause display device 310 to display a plurality of circular contrast zones and may receive inputs from touch sensitive screen 320. Testing unit 330 may communicate testing data to storage unit 340 via connection 332, but any other type of media or protocol may be used.

Referring now to FIGS. 4A-4D, various pluralities of circular contrast zones utilized in conjunction with a touch sensitive screen, such as touch sensitive screen 320, are illustrated.

Figure 4A:
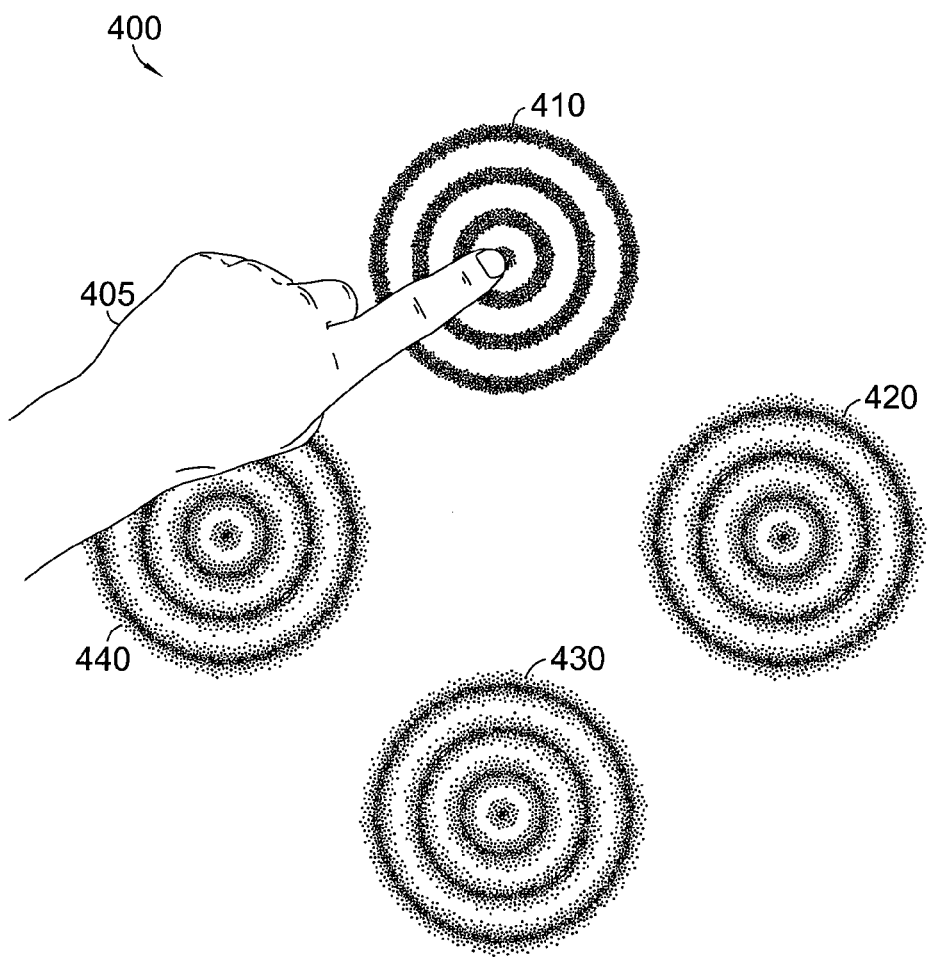
FIGS. 4A-4D illustrate various touch screen contrast sensitivity testing or training systems in accordance with the present invention.

Referring now to FIG. 4A, a plurality 400 of circular contrast zones may comprise a top contrast zone 410, a right contrast zone 420, a bottom contrast zone 430, and a left contrast zone 440. In the example illustrated in FIG. 4A, top contrast zone 410 possesses the highest contrast pattern of the plurality 400 of circular contrast zones. Subject (not illustrated) may select top contrast zone 410 by touching the screen where top contrast zone 410 is displayed, for example by using the hand 405 of subject.

Figure 4B:
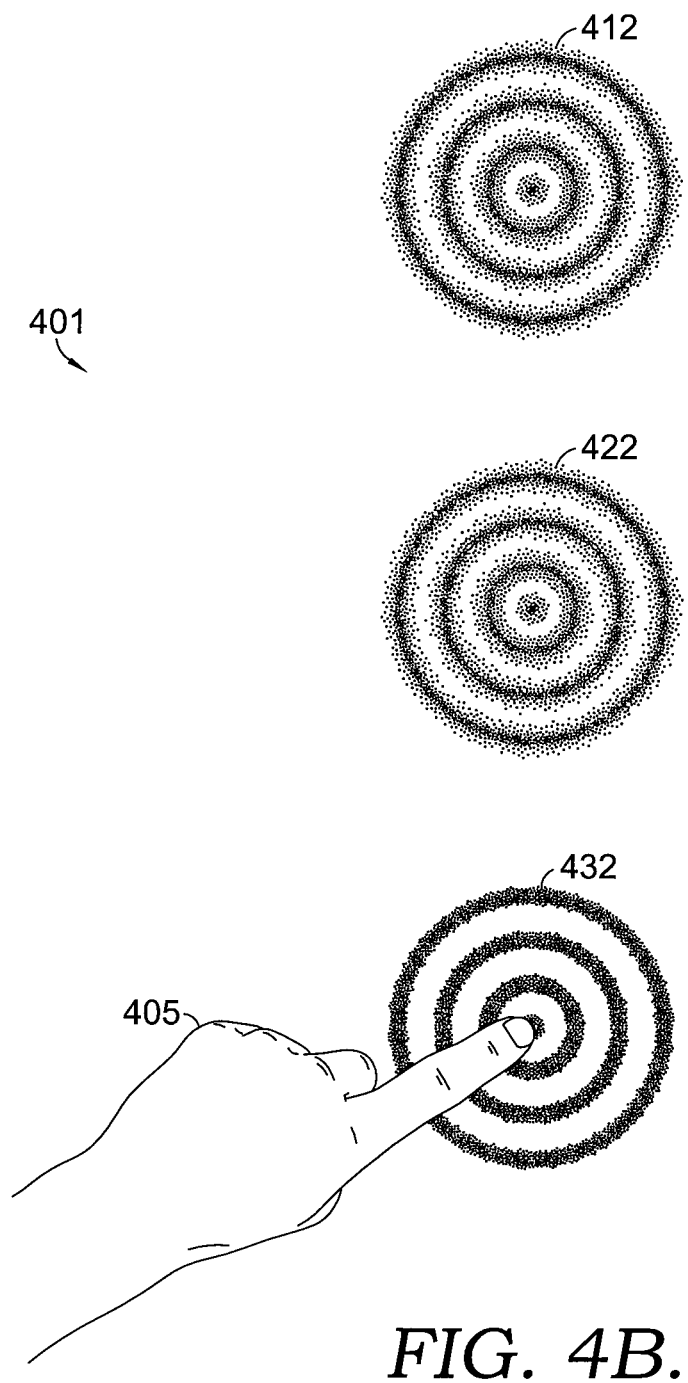

Referring now to FIG. 4B, a further plurality 401 of circular contrast zones is illustrated. Plurality 401 of circular contrast zones may comprise top contrast zone 412, middle contrast zone 422, and bottom contrast zone 432. In the example illustrated in FIG. 4B, bottom contrast zone 432 possesses the higher contrast pattern than the other circular contrast zones of plurality 401. Subject (not illustrated) may select bottom contrast zone 432 by using hand 405 to touch the displayed bottom contrast zone 432.

Figure 4C:
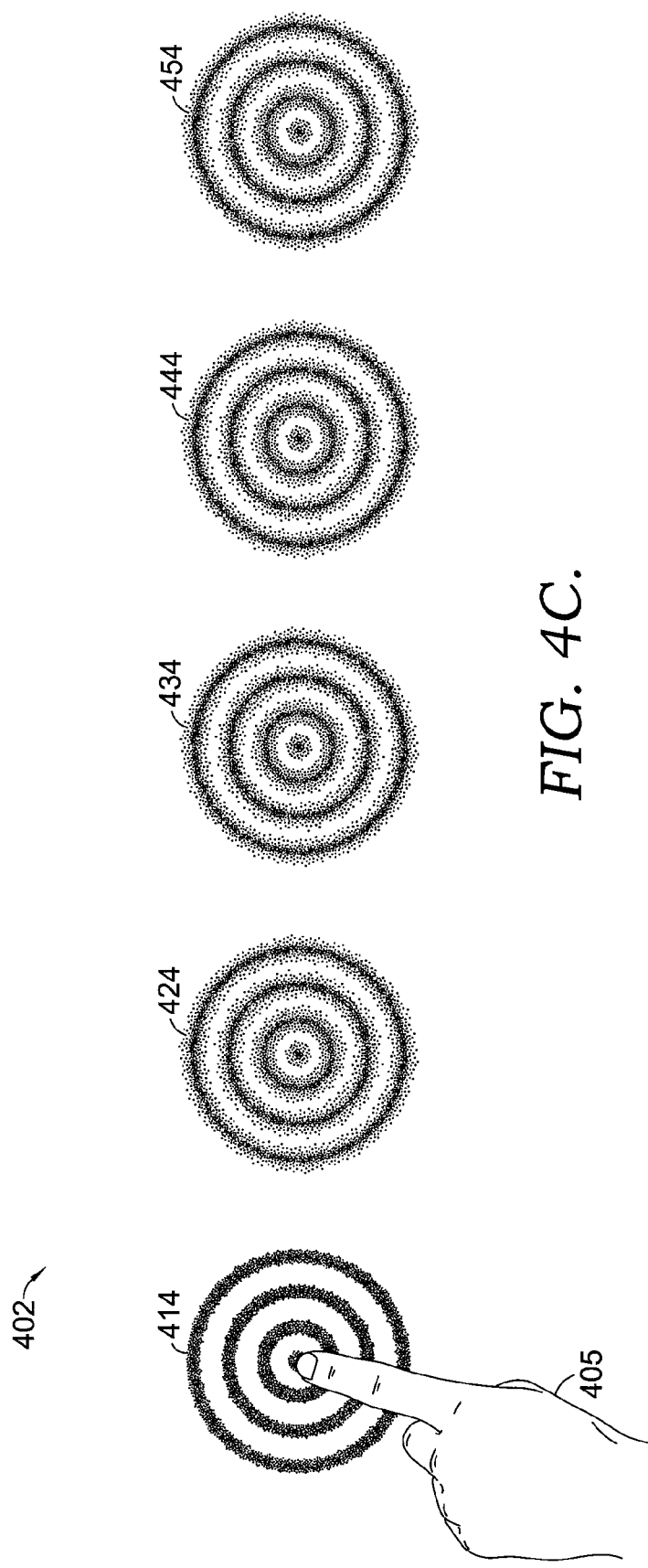

Referring now to FIG. 4C, a further plurality 402 of circular contrast zones is illustrated. Plurality 402 comprises, from left to right, a first contrast zone 414, a second contrast zone 434, a third contrast zone 434, a fourth circular zone 444, and a fifth contrast zone 454. In the example illustrated in FIG. 4C, first contrast zone 414, which is the left-most of plurality 402 of circular contrast zones, possesses a higher contrast pattern than the other circular contrast zones of plurality 402. Subject (not illustrated) may select first contrast zone 414 by touching the displayed first contrast zone 414.

Figure 4D:
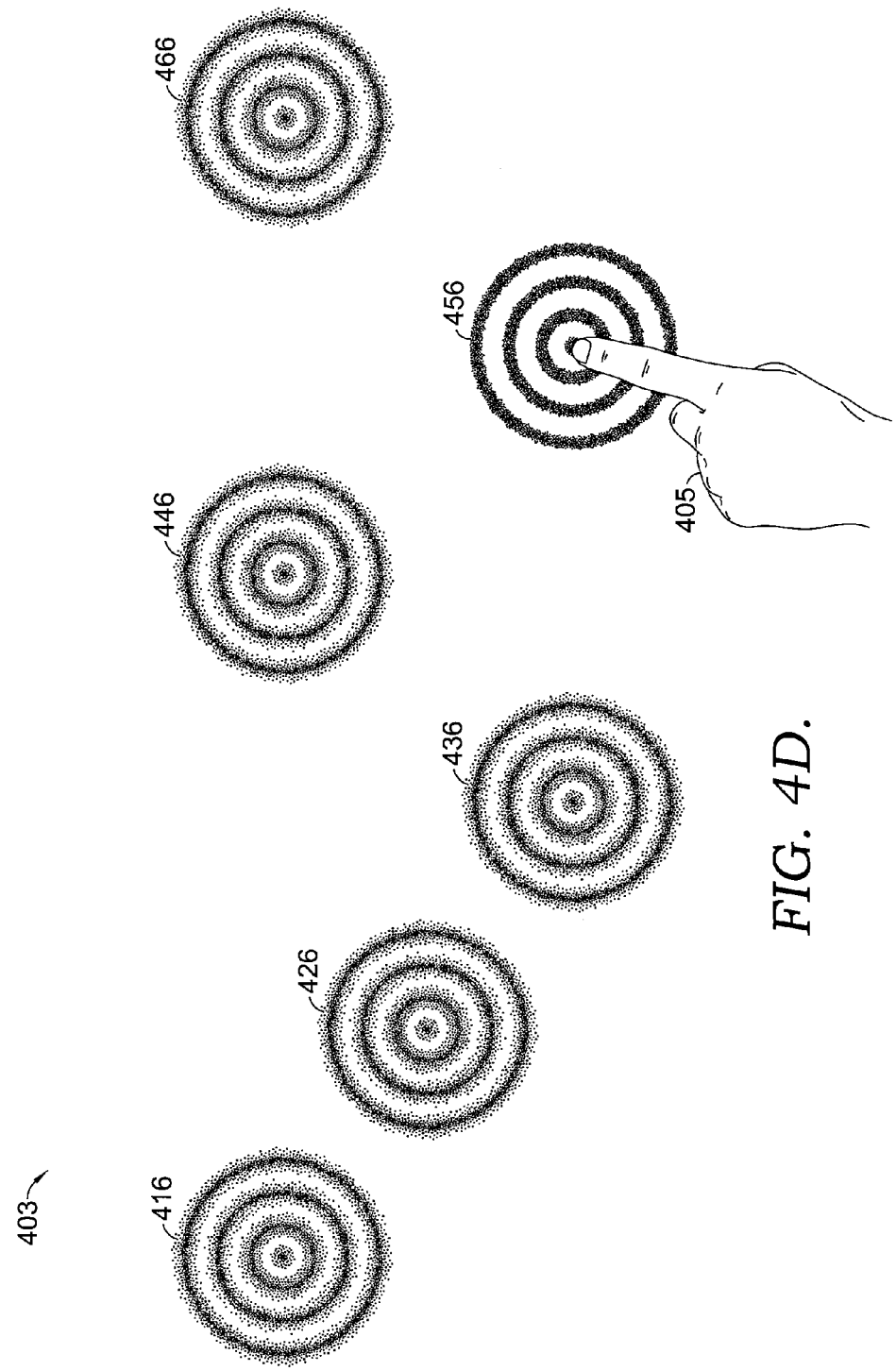

Referring now to FIG. 4D, a further plurality 403 of circular contrast zones is illustrated. Plurality 403 of circular contrast zones are distributed spatially in a random or pseudorandom pattern and comprises, moving generally from left to right, first contrast zone 416, second contrast zone 426, third contrast zone 436, fourth contrast zone 446, fifth contrast zone 456, and sixth contrast zone 466. In the example illustrated in FIG. 4D, fifth contrast zone 456 possesses a higher contrast pattern than the other circular contrast zones of plurality 403. Subject (not illustrated) may register the selection of fifth contrast zone 456 by touching the display fifth contrast zone using hand 405.

Figure 5:
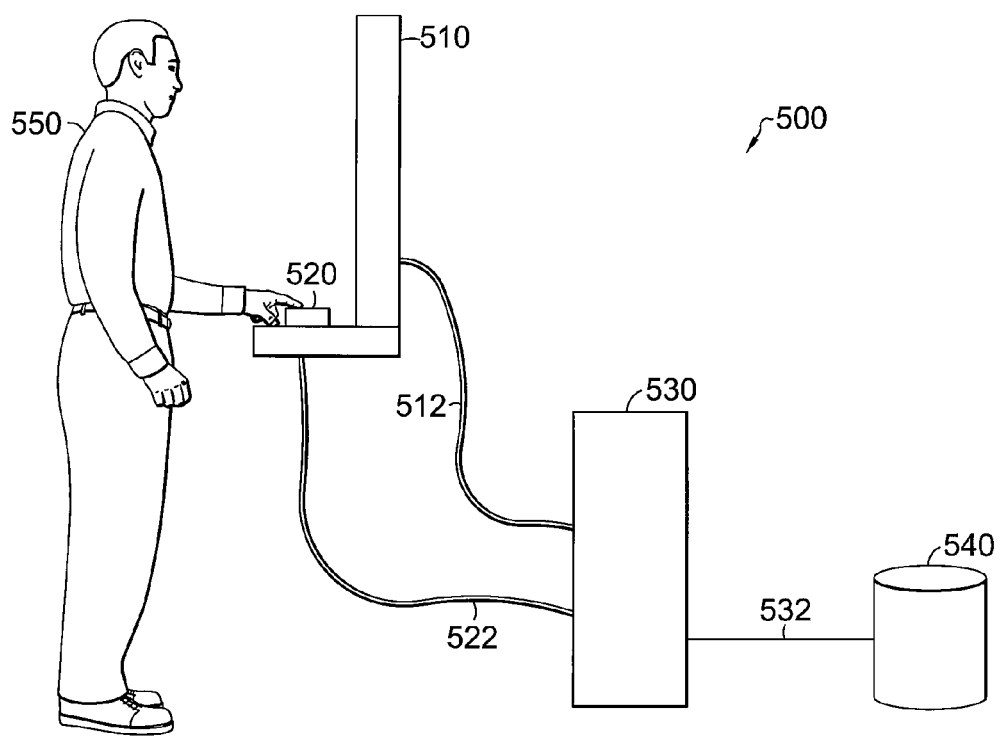
FIG. 5 illustrates a further system for testing or training contrast sensitivity in accordance with the present invention.

Referring now to FIG. 5, a further system 500 for contrast sensitivity testing or training in accordance with the present invention is illustrated. System 500 may comprise a display device 510 capable of displaying circular contrast zones to subject 550. Subject 550 may register the selection of one of the plurality of circular contrast zones displayed on display device 510 using keypad 520, which may comprise a plurality of keys, buttons, or the like. Testing unit 530 may communicate with display device 510 to cause it to display a plurality of circular contrast zones. While referred to as a "testing unit" or a "test unit" herein, testing unit 530 may be used for testing and/or training contrast sensitivity. Testing unit 530 may likewise communicate with keypad 520 using connection 522 to receive inputs from keypad 520 indicating that subject 550 has registered an input selecting one of the circular contrast zones displayed on display device 510. Testing unit 530 may communicate testing data to storage device 540 via connection 532.

Figure 6A:
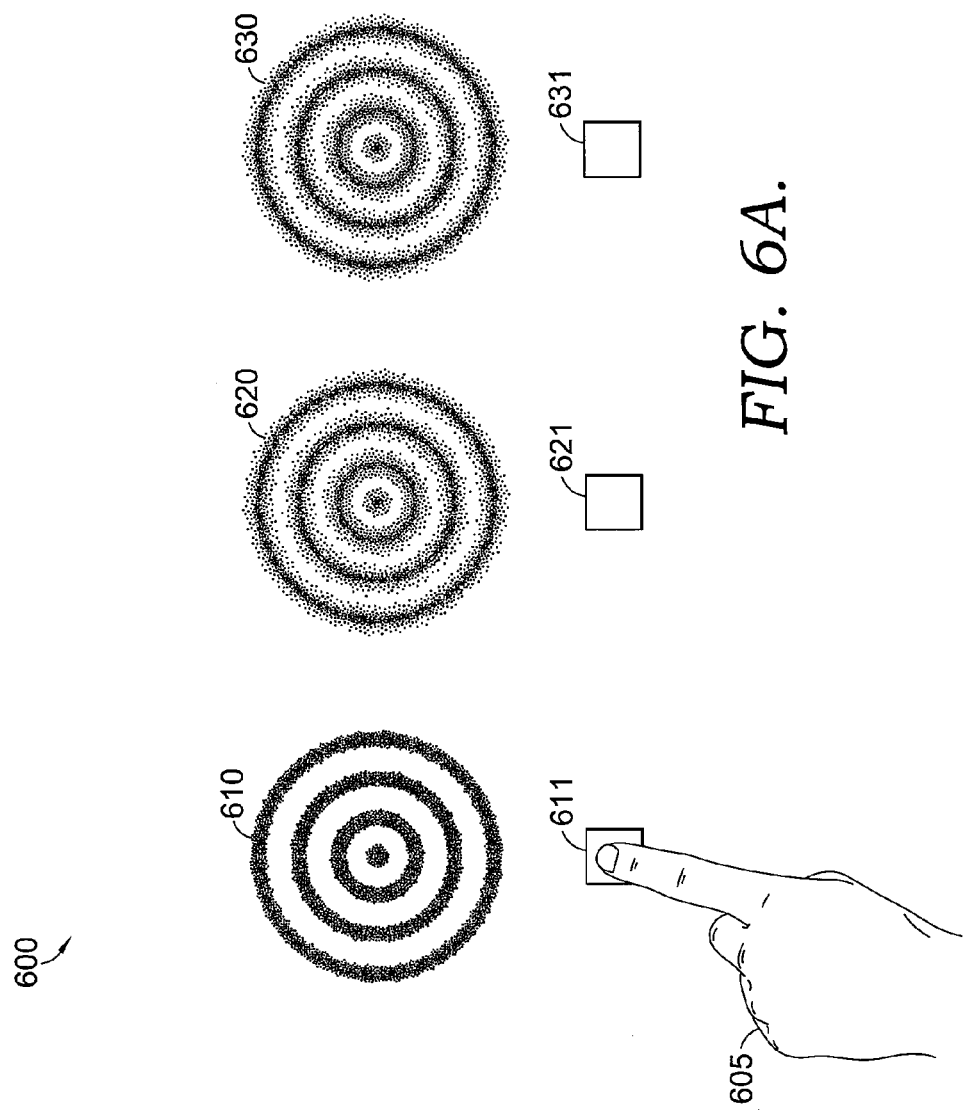
FIGS. 6A-6C illustrate contrast sensitivity testing or training systems in accordance with the present invention utilizing buttons.
Figure 6B:
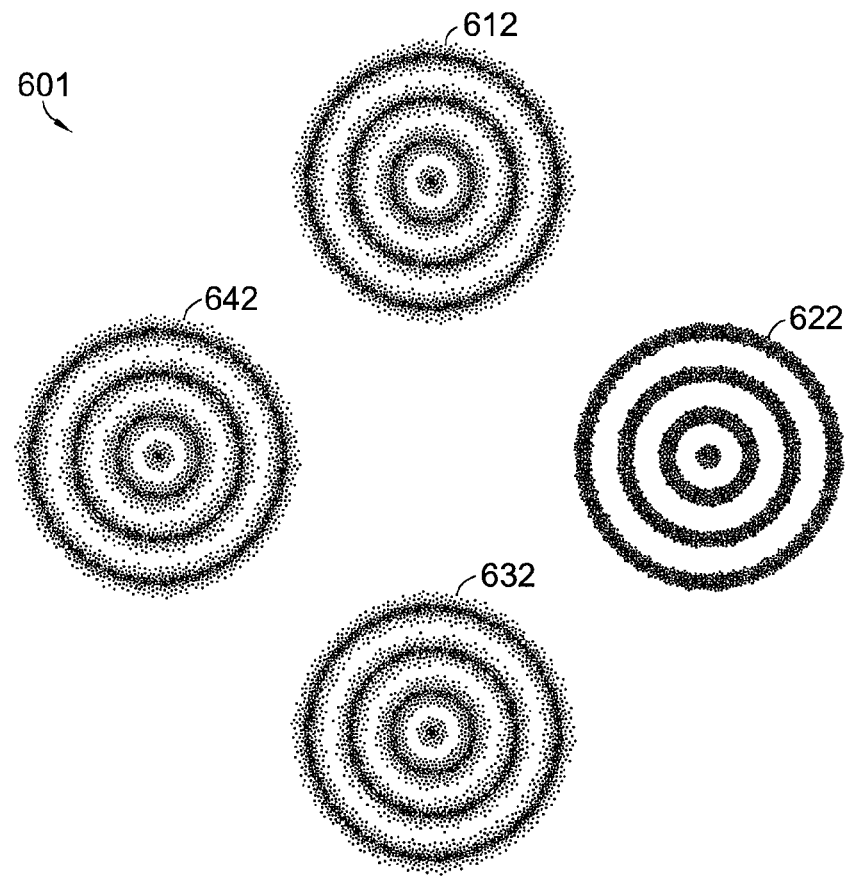
Figure 6B:
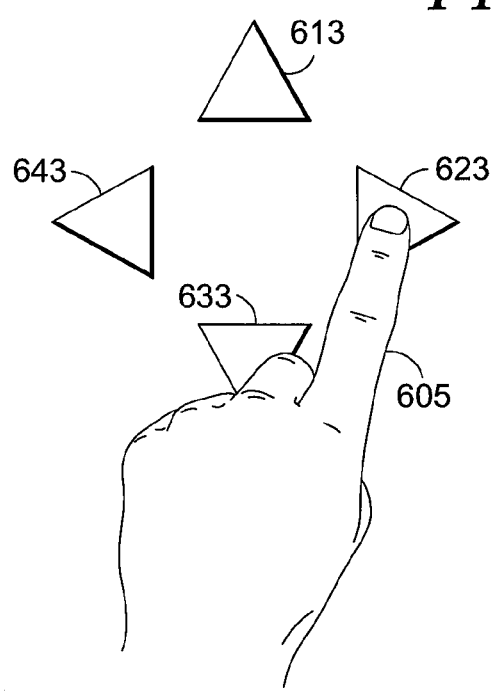
Figure 6C:
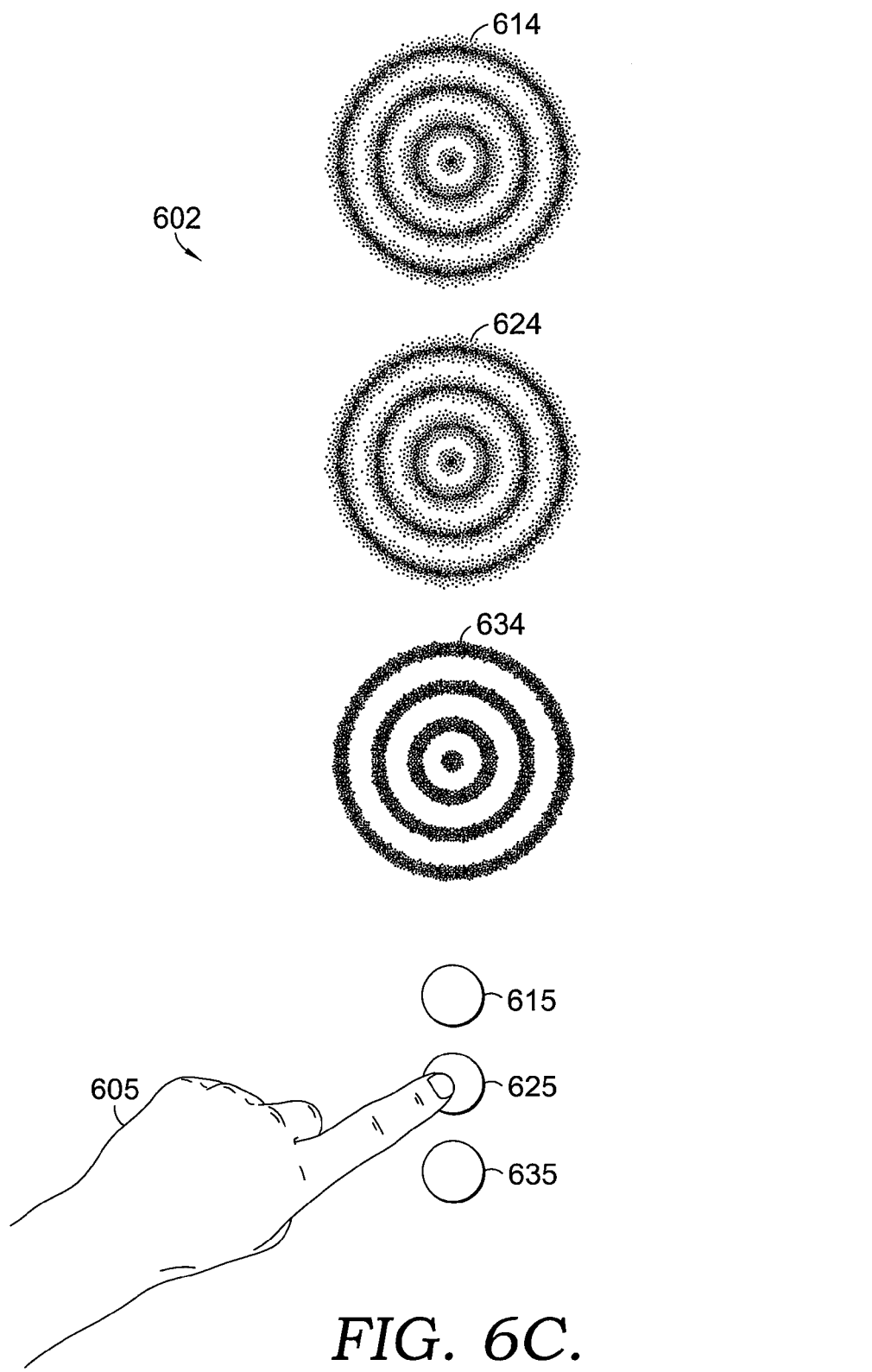

Referring now to FIG. 6A-6C, various configurations of keypads and circular contrast zones for use with system 500 are illustrated. Any arrangement, size, shape, configuration, and sort of buttons and/or keys may be utilized with the present invention besides those illustrated in the examples of FIGS. 6A-6C. The buttons or keys utilized in conjunction with the present invention need not be physical buttons or keys, but may also be "soft keys" such as may be utilized as part of a touch sensitive screen.

Referring now to FIG. 6A, a plurality 600 of circular contrast zones may comprise a left contrast zone 610, a middle contrast zone 620, and a right contrast zone 630. A keypad may provide a left key 611, a middle key 621, and a right key 631. In the example illustrated in FIG. 6A, left contrast zone 610 possesses a higher contrast pattern than the other circular contrast zones of plurality 600. Subject (not illustrated) may register the selection of left circular contrast zone 610 by engaging left button 611 using hand 605.

Referring now to FIG. 6B, a further plurality of circular contrast zones is illustrated. Plurality 601 of circular contrast zones may comprise a top contrast zone 612, a right contrast zone 622, a bottom contrast zone 632, and a left contrast zone 642. In the example illustrated in FIG. 6B, right contrast zone 622 possesses a higher contrast pattern than the other circular contrast zones of plurality 601 of circular contrast zones. In the example illustrated in FIG. 6B, a plurality of keys providing a directional orientation may be provided, in this example and up-key 613, a right-key 623, a down-key 633, and left-key 643. Subject (not illustrated) may indicate a selection of a circular contrast zone, in this example the right contrast zone 622 by engaging a key, in this example right key 623, using hand 605.

Referring now to FIG. 6C, a further plurality 602 of circular contrast zones in accordance with the present invention is illustrated. Plurality 602 may comprise a top contrast zone 614, a middle contrast zone 624, and a bottom contrast zone 634. Subject (not illustrated) may register an input selecting one of the plurality 602 of circular contrast zones using a top-button 615, a middle-button 625, or a bottom-button 635. In the example illustrated in FIG. 6C, middle contrast zone 624 possesses a higher contrast pattern than the other circular contrast zones of plurality 602. Subject (not illustrated) may indicate the selection of middle contrast zone 624 by engaging middle-button 625 using hand 605.

Figure 7:
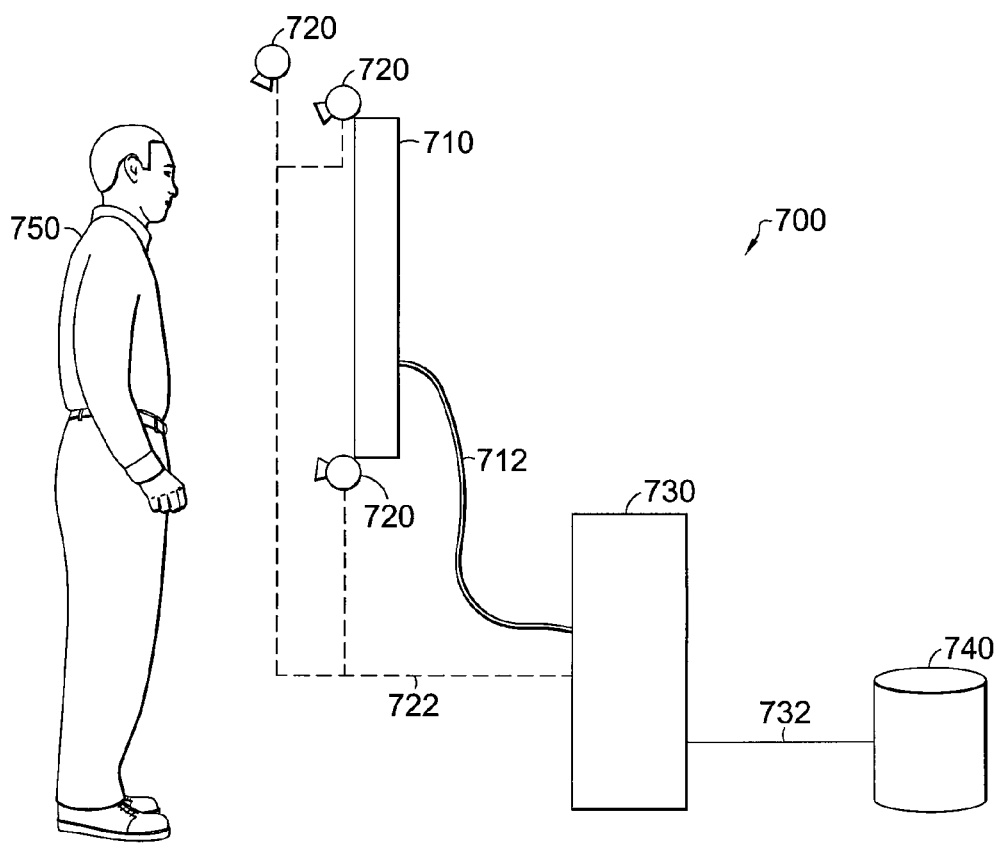
FIG. 7 illustrates a further system for testing or training contrast sensitivity in accordance with the present invention.

Referring now to FIG. 7, a further system 700 for testing or training the contrast sensitivity of a subject 750 is illustrated. Circular contrast zones may be displayed to subject 750 on display device 710. Subject 750 may register a selection of a circular contrast zone displayed on display device 710 using gestures or movements. In the example of FIG. 7, cameras 720 may be utilized to detect motions or gestures by subject 750, possibly in conjunction with software operating on testing unit 730. Of course, a variety of motion/gesture recognition systems currently exist and are under development, and any of these technologies may be utilized in conjunction with contrast sensitivity testing in accordance with the present invention, such as the example illustrated in FIG. 7. Camera 720 may communicate with wireless link 722, although any other kind of wired or wireless connection may be used. Testing unit 730 is connected to display device 710 via connection 712, although any type of wired or wireless connection may be used. While referred to as a "testing unit" or a "test unit" herein, testing unit 730 may be used for testing and/or training contrast sensitivity. Testing unit 730 may control the display of circular contrast zones on display device 710 and receive and/or process data from cameras 720 as part of receiving an input or processing gesture recognition data. Testing unit 730 may transmit data to storage device 740 via connection 732 for storage.

Referring now to FIGS. 8A-8D, various arrangements of circular contrast zones and input receipts using gesture recognition are illustrated.

Figure 8A:
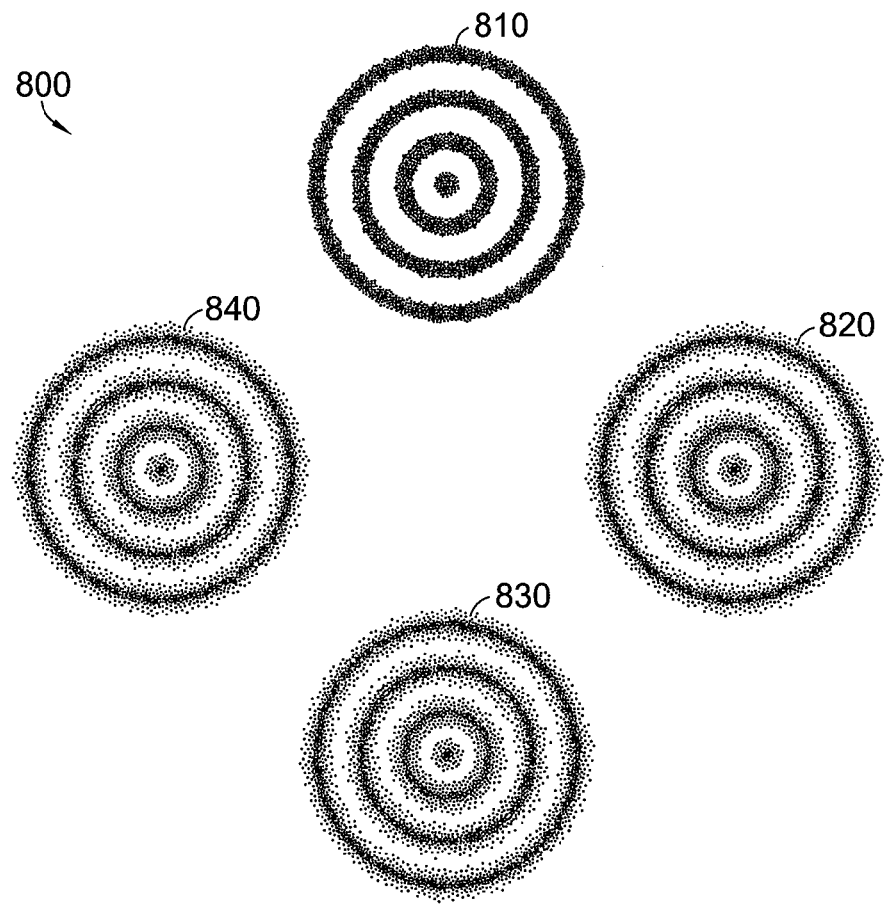
FIGS. 8A-8D illustrate various pluralities of circular contrast zones and gestures using gesture recognition input in accordance with the present invention.
Figure 8A:
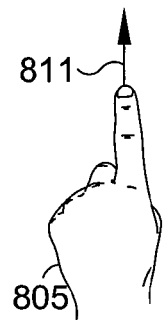

Referring to FIG. 8A, a plurality 800 of circular contrast zones may comprise a top contrast zone 810, a right contrast zone 820, a bottom contrast zone 830, and a left contrast zone 840. In the example of FIG. 8A, top contrast zone 810 possesses a higher contrast pattern than the other contrast zones of plurality 800. Subject (not illustrated) may indicate the selection of top contrast zone 810 by gesturing in an upward direction 821 using hand 805.

Figure 8B:
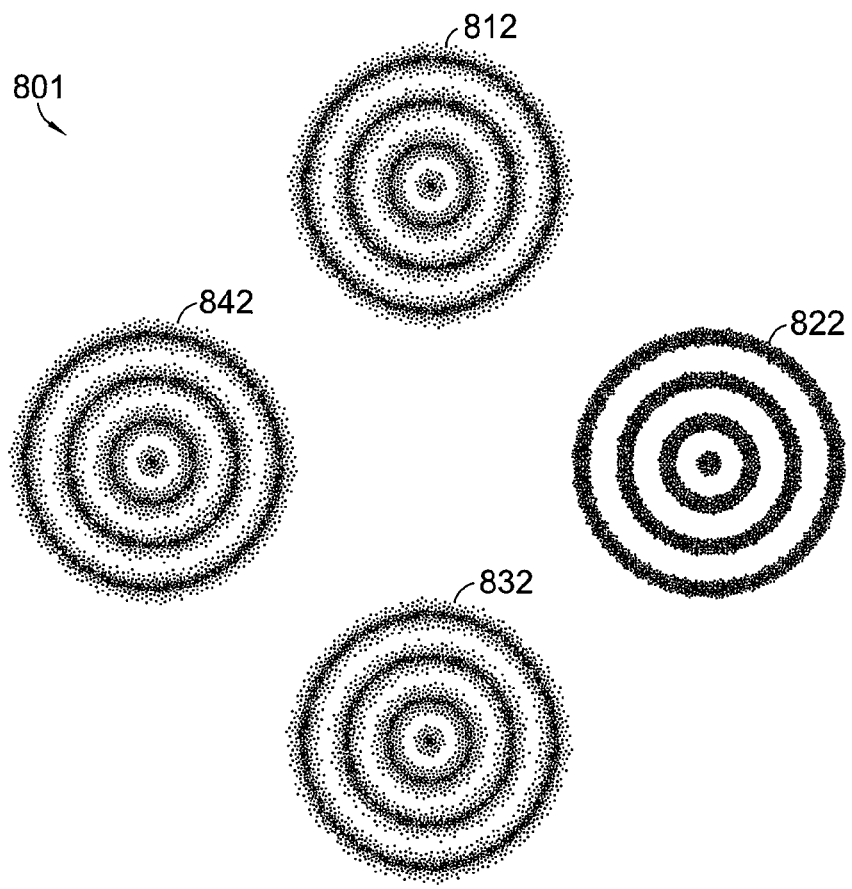
Figure 8B:
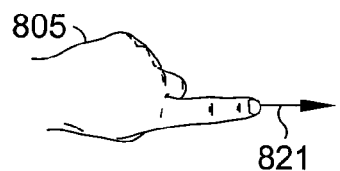

Referring now to FIG. 8B, a plurality 801 of circular contrast zones may comprise a top contrast zone 812, a right contrast zone 822, a bottom contrast zone 832, and a left contrast zone 842. In the example of FIG. 8B, right contrast zone 822 possesses a higher contrast pattern than the other circular contrast zones of plurality 801. Subject (not illustrated) may indicate the selection of right contrast zone 822 by gesturing in a rightward direction 831 using hand 805.

Figure 8C:
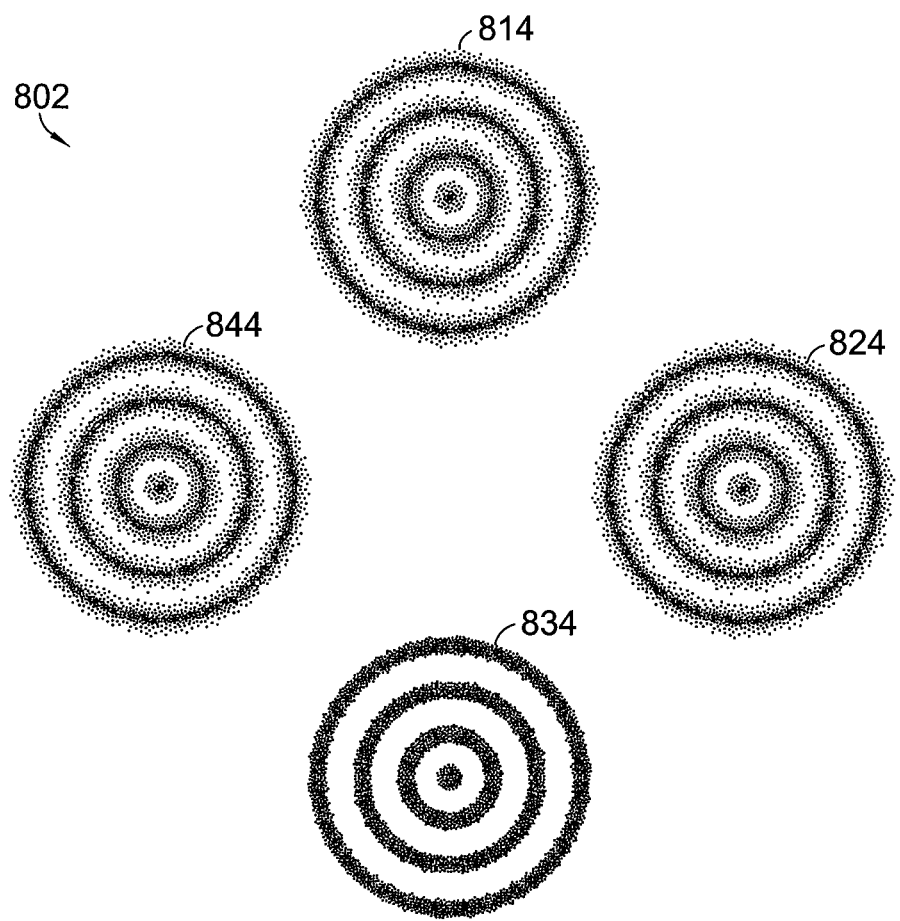
Figure 8C:
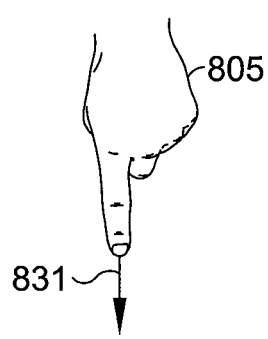

Referring now to FIG. 8C, a plurality 802 of circular contrast zones is illustrated. Plurality 802 comprises top contrast zone 814, a right contrast zone 824, a bottom contrast zone 834, and left contrast zone 844. In the example illustrated in FIG. 8C, bottom contrast zone 834 possesses a higher contrast pattern than the other circular contrast zones of plurality 802. Subject (not illustrated) may indicate the selection of bottom contrast zone 834 by gesturing in a downward direction 841 using hand 805.

Figure 8D:
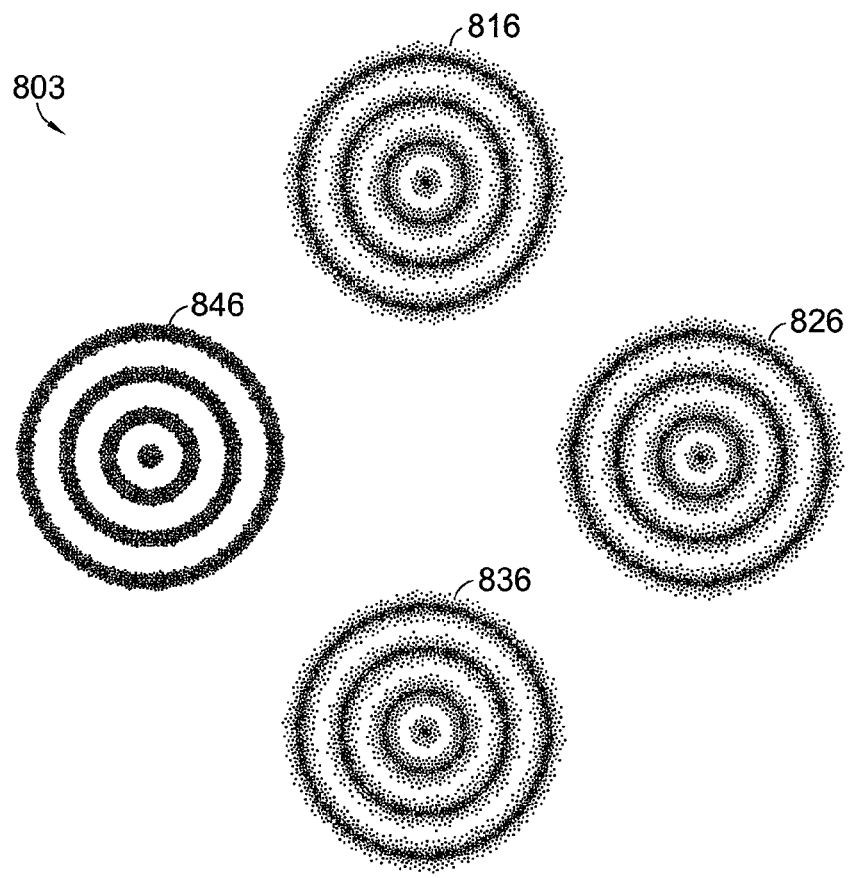
Figure 8D:
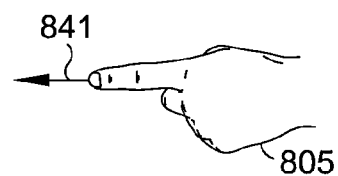

Referring now to FIG. 8D, a plurality 803 of circular contrast zones is illustrated. Plurality 803 may comprise a top contrast zone 816, a right contrast zone 826, a bottom contrast zone 836, and a left contrast zone 846. In the example of FIG. 8D, left contrast zone 846 possesses a higher contrast pattern than the other circular contrast zones of plurality 803. Subject (not illustrated) may indicate the selection of left contrast zone 846 by gesturing in a leftward direction 841 using hand 805.

Figure 9:
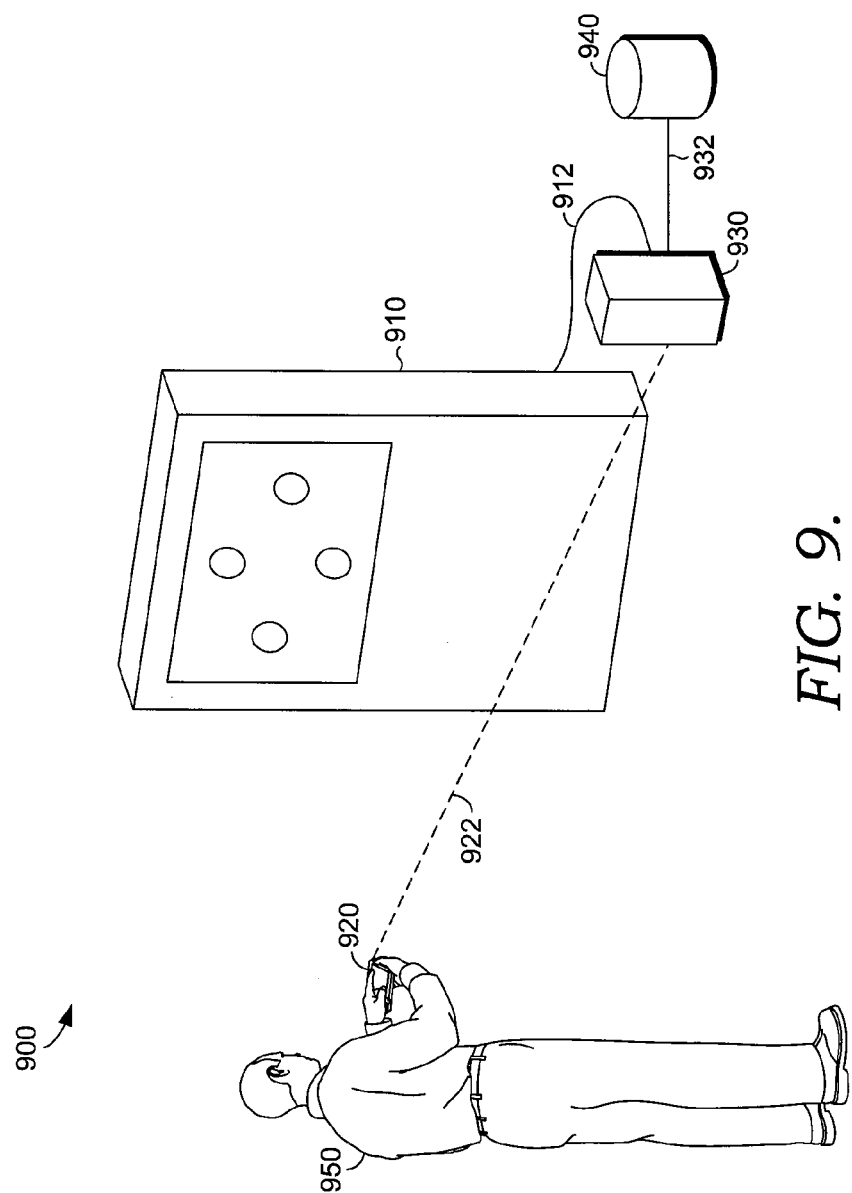
FIG. 9 illustrates a further system for testing or training contrast sensitivity in accordance with the present invention utilizing a multi-touch input device.

Referring now to FIG. 9, a further system 900 for testing and/or training the contrast sensitivity of a subject 950 is illustrated. Circular contrast zones may be displayed to subject 950 on display device 910. Subject 950 may register a selection of a circular contrast zone displayed on display device 910 using a multi-touch device 920, such as in iPod touch. Multi-touch device 920 may connect to test unit 930 over a wireless link 922. Wireless link 922 may utilize Bluetooth, 802.11, or any other standard or nonstandard wireless communication protocol. Testing unit 930 may connect to display device 910 via connection 912. While referred to as a "testing unit" or a "test unit" herein, testing unit 930 may be used for testing and/or training contrast sensitivity. Testing unit 930 may control the display of circular contrast zones on display device 910 when inputs are registered by subject 950. Testing unit 930 may transmit data to storage device 940 via connection 932 for storage.

Referring now to FIGS. 10A-10D, various arrangements of circular contrast zones and input receipts using a multi-touch device are illustrated.

Figure 10A:
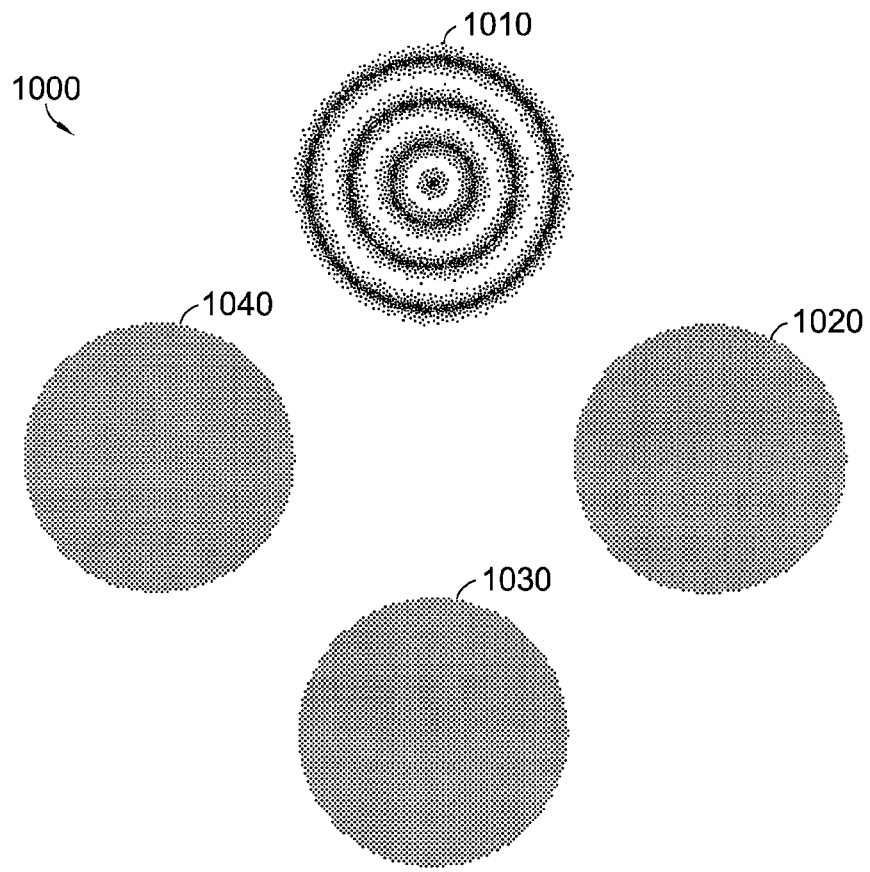
FIGS. 10A-10D illustrate various pluralities of circular contrast zones and inputs using a multi-touch input device in accordance with the present invention.
Figure 10A:
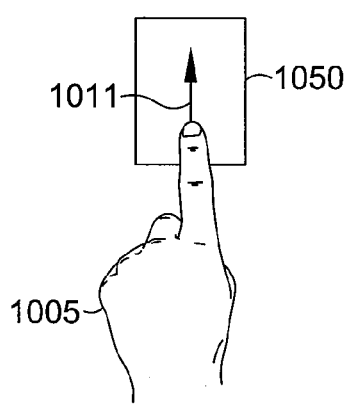

Referring now to FIG. 10A, a plurality 1000 of circular contrast zones may comprise a top contrast zone 1010, a right contrast zone 1020, a bottom contrast zone 1030, and a left contrast zone 1040. In the example of FIG. 10A, top contrast zone 1010 possesses a higher contrast pattern than the other contrast zones of plurality 1000. In the example of FIG. 10A, right contrast zone 1020, bottom contrast zone 1030, and left contrast zone 1040 possess zero contrast, in that they are uniform in pigmentation. In the example of FIG. 10A, subject (not illustrated) may indicate the selection of top contrast zone 1010 by contacting multi-touch device 1050 in an upward direction 1011 using hand 1005.

Figure 10B:
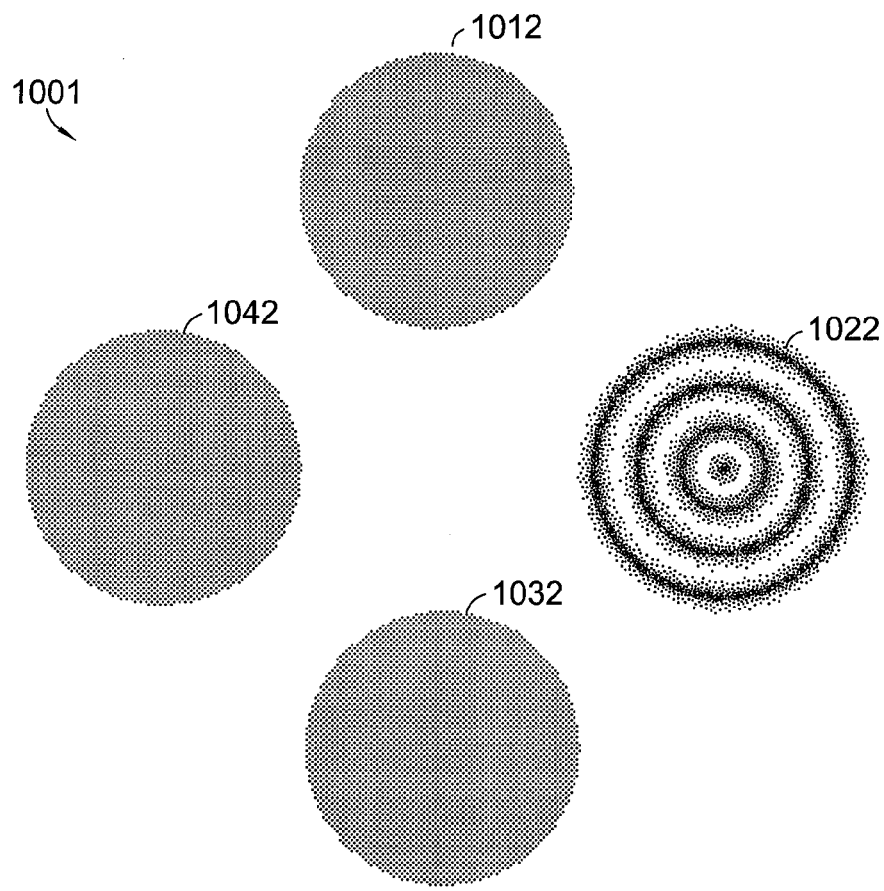
Figure 10B:
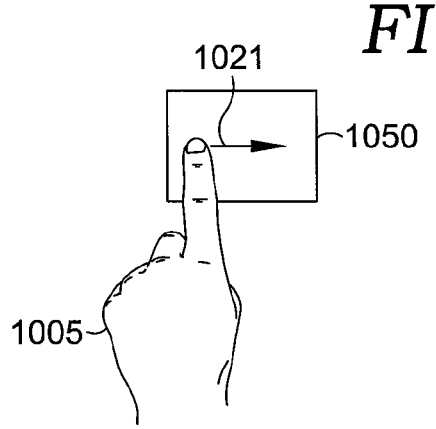

Referring now to FIG. 10B, a plurality 1001 of contrast circular zones may comprise a top contrast zone 1012, a right contrast zone 1022, a bottom contrast zone 1032, and a left contrast zone 1042. In the example of FIG. 10B, right contrast zone 1022 possesses a higher contrast pattern than the other circular contrast zones of plurality 1001. Subject (not illustrated) may indicate the selection of right contrast zone 1022 by contacting multi-touch device 1050 in a rightward direction 1021 with hand 1005.

Figure 10C:
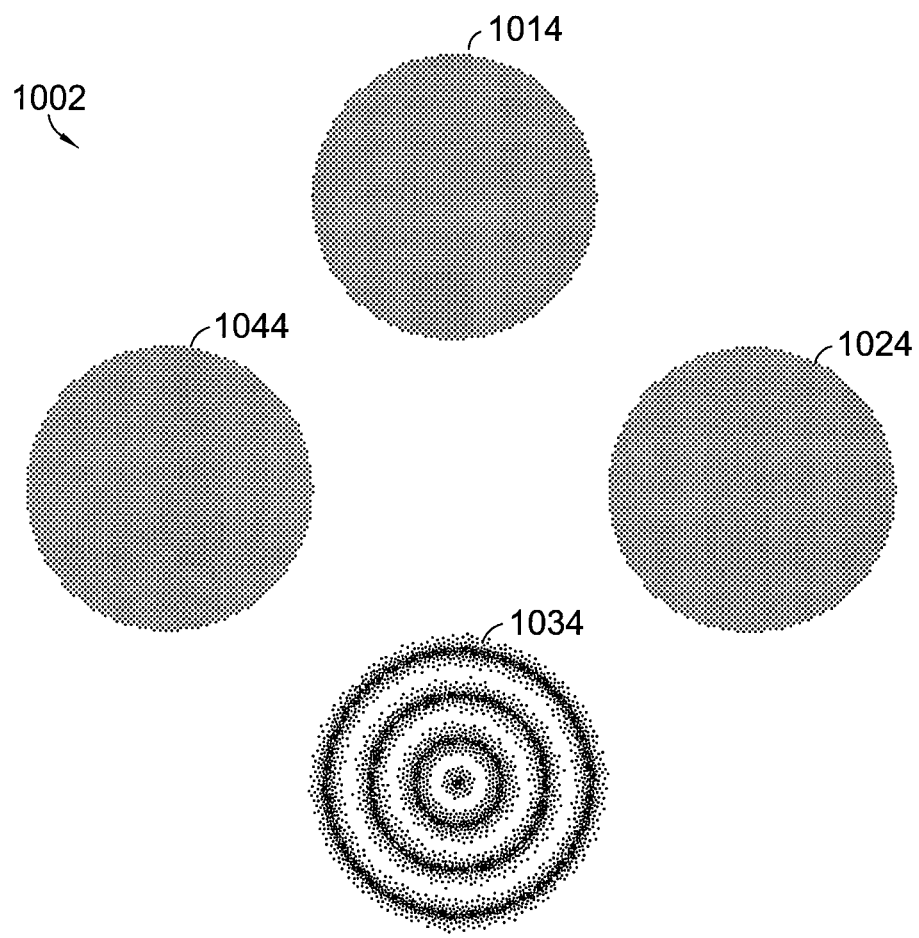
Figure 10C:
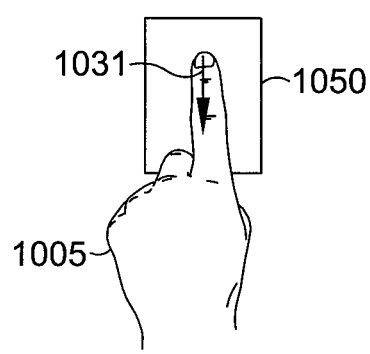

Referring now to FIG. 10C, a plurality 1002 of circular contrast zones is illustrated. Plurality 1002 comprises top contrast zone 1014, right contrast zone 1024, bottom contrast zone 1034, and left contrast zone 1044. In the example illustrated in FIG. 10C, bottom contrast zone 1034 possesses a higher contrast pattern than the other circular contrast zones of plurality 1002. Subject (not illustrated) may indicate the selection of bottom contrast zone 1034 by contacting multi-touch device 1050 in a downwards direction 1031 with hand 1005.

Figure 10D:
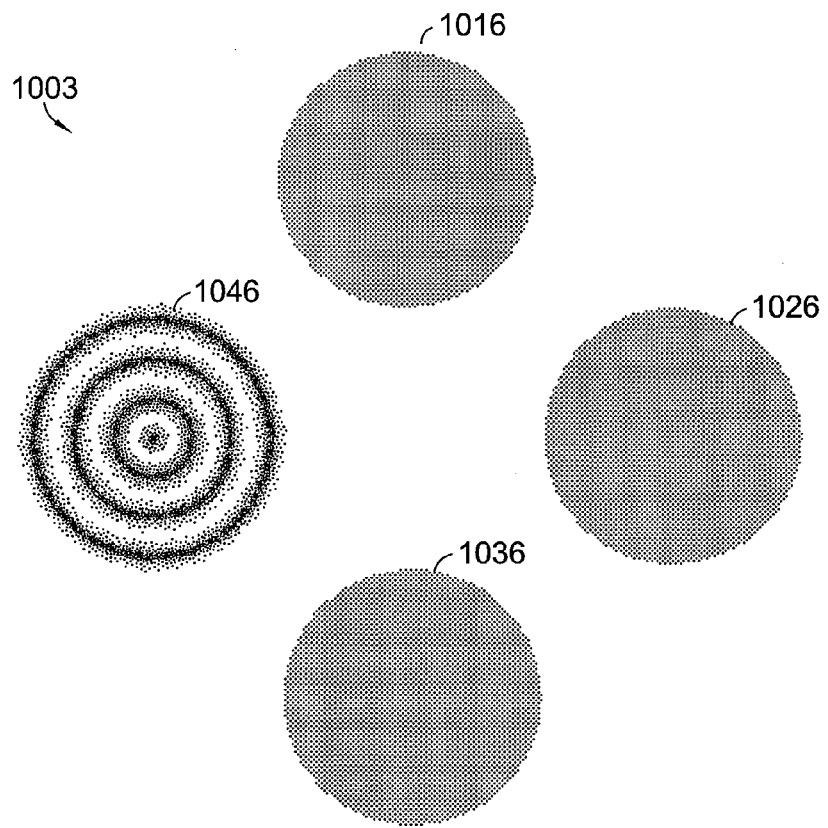
Figure 10D:
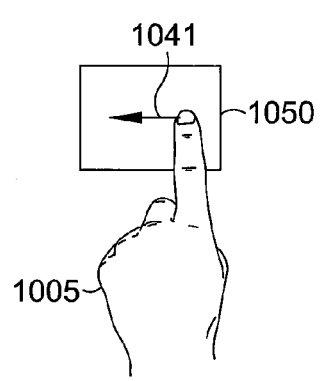

Referring now to FIG. 10D, a plurality 1003 of circular contrast zones is illustrated. Plurality 1003 may comprise a top contrast zone 1016, a right contrast zone 1026, a bottom contrast zone 1036, and a left contrast zone 1046. In the example of FIG. 10D, left contrast zone 1046 possesses a higher contrast pattern than the other contrast zones of plurality 1003. Subject (not illustrated) may indicate the selection of left contrast zone 1046 by contacting multi-touch device 1050 in a leftward direction 1041 with hand 1005.

Figure 11:
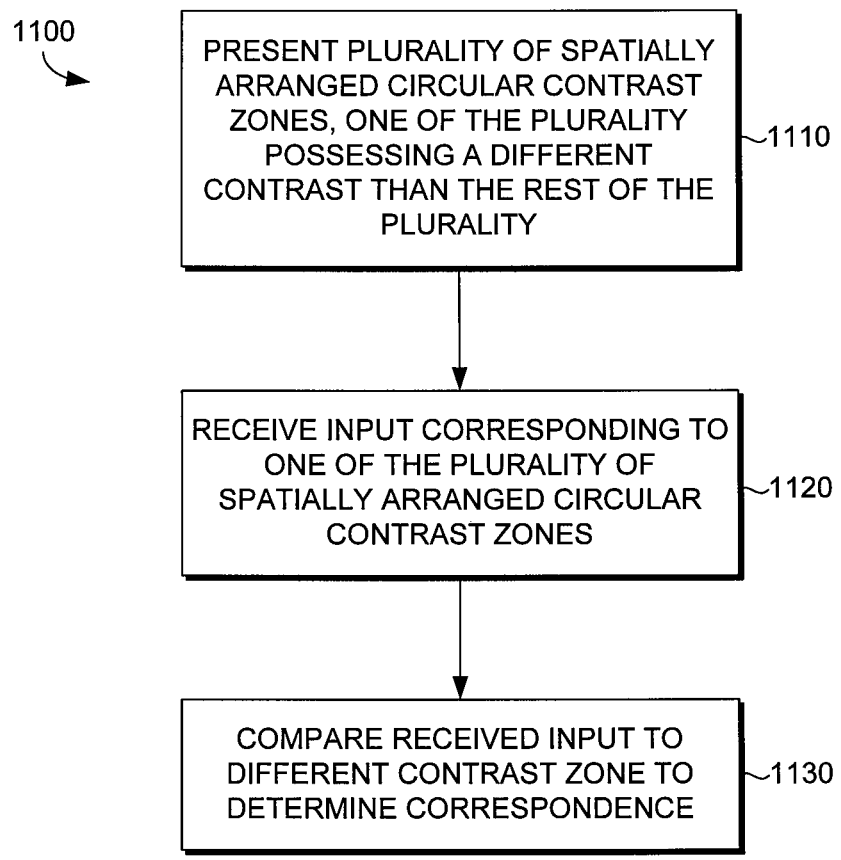
FIG. 11 illustrates a method for testing or training contrast sensitivity in accordance with the present invention.

Referring now to FIG. 11, a method 1100 for testing or training contrast sensitivity in accordance with the present invention is illustrated. In step 1110 a plurality of spatially arranged circular contrast zones are presented to a subject, one of the plurality of circular contrast zones possessing a different contrast then the rest of the plurality. In step 1120, an input is received from a subject corresponding to one of the plurality of spatially arranged circular contrast zones. In step 1130, the received input is compared to the contrast zone having a different contrast pattern to determine the correspondence between the input and the differing circular contrast zone. Step 1130 effectively determines whether the subject correctly perceived the presented plurality of circular contrast zones.

Figure 12:
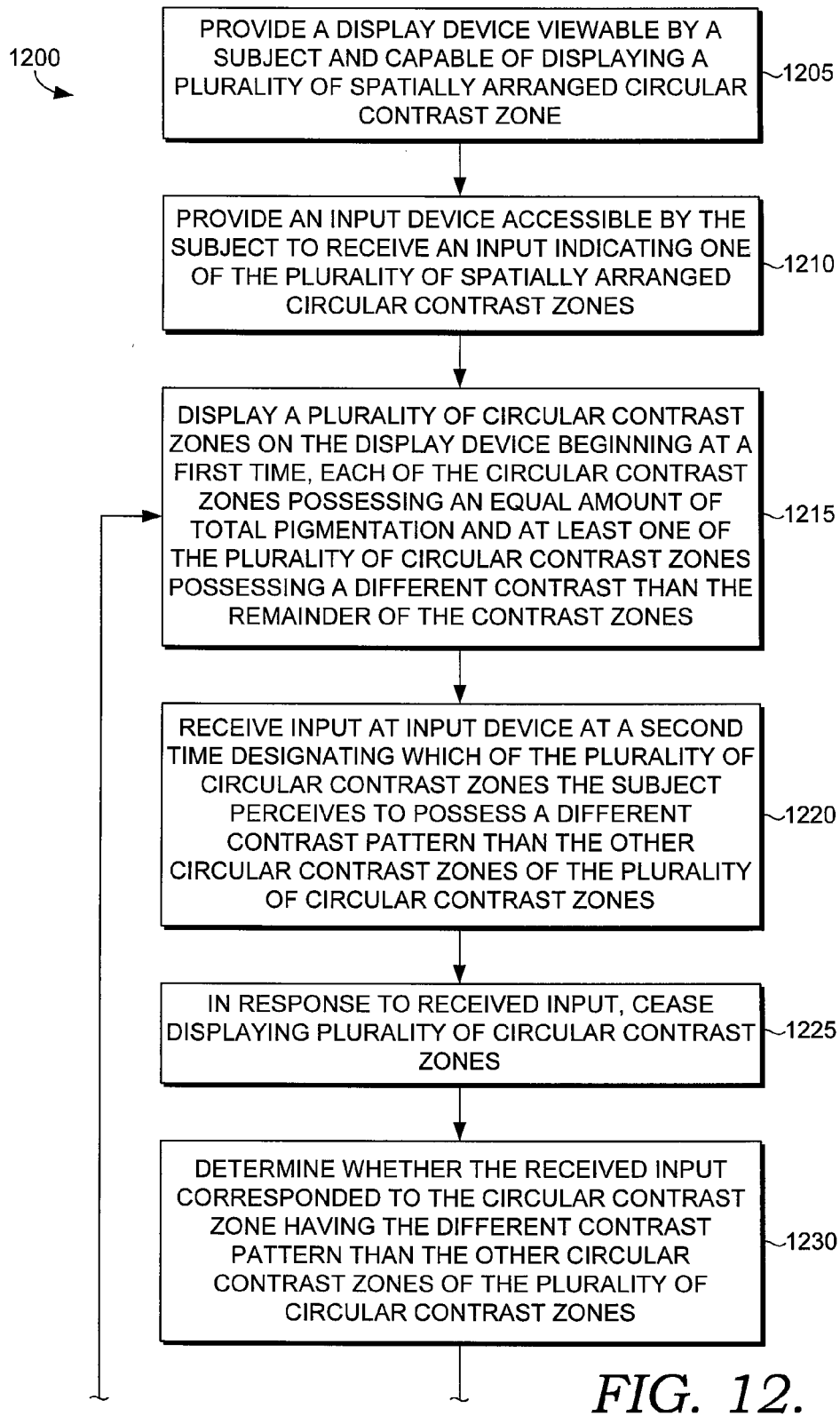
FIG. 12 illustrates a further method for testing or training contrast sensitivity in accordance with the present invention.
Figure 12:
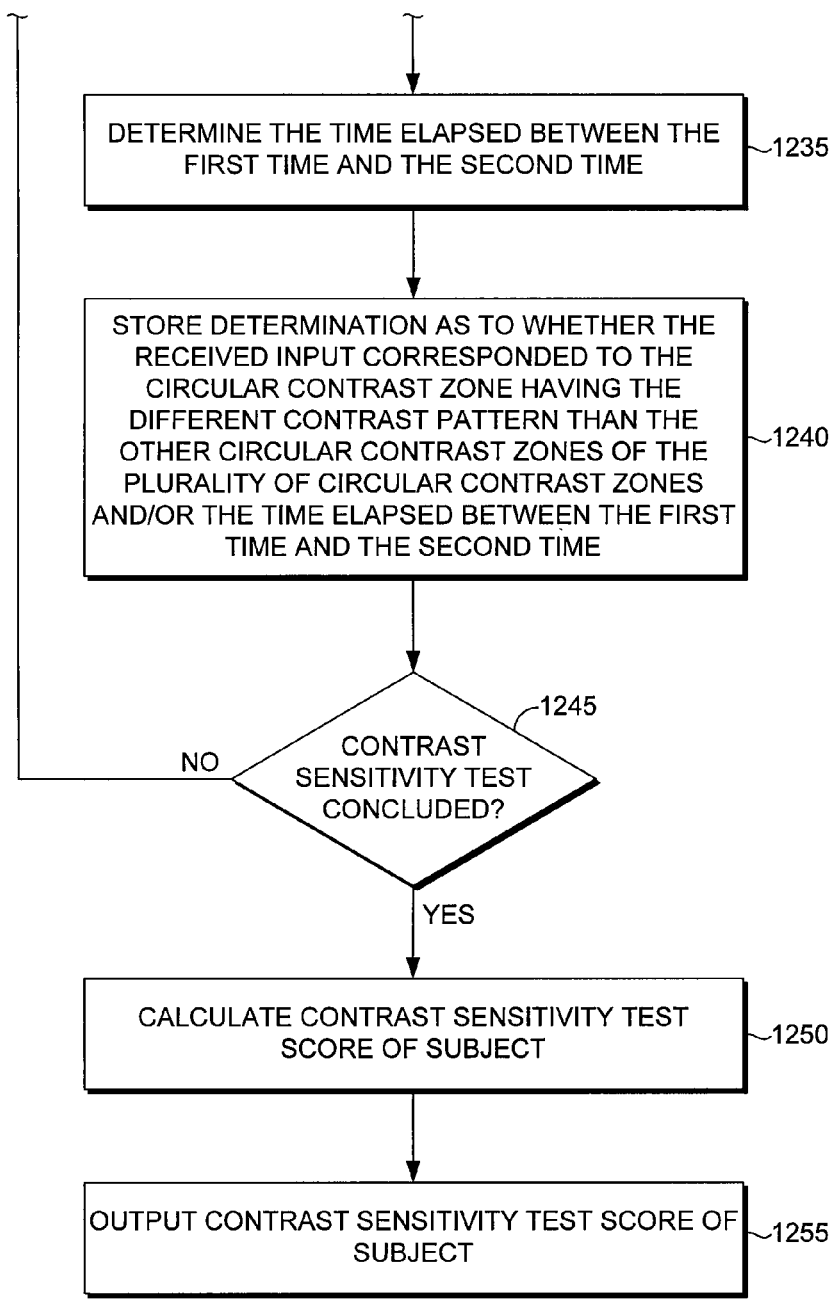

Referring now to FIG. 12, a further method 1200 for testing or training the contrast sensitivity of a subject is illustrated. In step 1205 a display device is provided that is viewable by a subject and capable of displaying a plurality of spatially arranged circular contrast zones. In step 1210, an input device is provided that is accessible by the subject to receive an input from the subject indicating one of the plurality of spatially arranged circular contrast zones. For example, the input device provided may be capable of receiving any of a plurality of inputs, each of the inputs corresponding in a spatial fashion to one of the plurality of circular contrast zones via display device provided in step 1205 is capable of displaying.

In step 1215, a plurality of circular contrast zones are displayed on the display device beginning at a first time, each of the circular contrast zones possessing an equal amount of total pigmentation and at least one of the plurality of circular contrast zones possessing a different contrast than the remainder of the contrast zones. For example, in step 1215 a testing unit may cause the display device to display a top contrast zone, a right contrast zone, a bottom contrast zone, and a left contrast zone, with one of the contrast zones differing in its total contrast from the other contrast zones by having higher contrast than the other zones. For example, one contrast zone may possess a non-zero contrast, while the other contrast zones may possess zero contrast. Of course, more than one, or even all, of the contrast zones may have a non-zero contrast zone, with one contrast having a higher contrast than the other contrast zones. In step 1220, an input is received at the input device at a second time after the first time, the input designating which of the plurality of circular contrast zones the subject perceives to possess a different contrast pattern than the other circular contrast zones of the plurality of contrast zones displayed in step 1215. Any manner of input types, such as the examples described above with regard to FIGS. 1-10, may be used in conjunction with step 1220. In step 1225, in response to receiving an input step 1220, the displaying of the plurality of circular contrast zones ceases.

In step 1230, it is determined whether the received input corresponded to the circular contrast zone having the different contrast pattern than the other circular contrast zones of the plurality of circular contrast zones. Step 1230 provides a measure of the accuracy of the subject's contrast sensitivity. In step 1235, the time elapsed from the first time at which the plurality of circular contrast zones are first displayed and the second time at which an input is received is determined. Step 1235 provides a measure of the speed of the subject's contrast sensitivity. In step 1240, a determination is stored as to whether the received input corresponded to the circular contrast zone having the different contrast pattern than the other circular contrast zones. Step 1240 may additionally/alternatively store a measure of the time elapsed between the first time and the second time. The measures of accuracy and/or speed stored in step 1240 may be useful in both testing and training the contrast sensitivity of a subject.

In step 1245, a determination may be made as to whether the contrast sensitivity test/training session has been concluded. The result of the determination of 1245 may be based upon any of a number of possible considerations. For example, the contrast sensitivity test/training session may be designed to operate for ten iterations, possibly each at a different contrast differential between the one circular contrast zone having a different contrast than the other contrast zones. In such an example, the conclusion of step 1245 would be that the contrast sensitivity test/training session is not completed until it has been iterated ten times. Alternatively, a contrast sensitivity test/training session may be designed such that it increases in difficulty until the subject incorrectly identifies the circular contrast zone having a different contrast a certain number of times, which may be one or more. In this additional example, the determination of step 1245 would be based upon the accuracy of the input received in step 1220 and the determination of step 1230, possible in conjunction with prior iterations of these steps. A "stair step" methodology may alternatively be used whereby the first iteration presents a high contrast circular contrast zone, the next iteration(s) decreases the contrast a "full" step until an incorrect response is made, after an incorrect response is made contrast is increased a "half" step, and thereafter decreased by a "quarter" step is a correct response is received and increased by a "quarter" step if an incorrect response is received, and so on until a contrast difference in a "step" may vary. Any number of variations may be used in step 1245 to determine whether the contrast sensitivity test has concluded. If the result of step 1245 is a determination that the contrast sensitivity test has not concluded, method 1200 returns to step 1215 of displaying a plurality of circular contrast zones. The iteration of steps 1215 through 1240 may utilize different contrast patterns, and even different arrangements of circular contrast zones, possibly having different total numbers, than prior iterations, but need not. If the conclusion of step 1245 is that the contrast sensitivity test has concluded, method 1200 may proceed to step 1250.

In step 1250, a contrast sensitivity test score of the subject may be calculated. The contrast sensitivity test score calculated in step 1250 may simply comprise the number of correct responses of a subject, or may be more complicated. Such a test score may account for the degree of contrast of the circular contrast zones during the test, the time elapsed between time one and time two and any other factors.

In step 1255, the contrast sensitivity test score for the subject may be output. Step 1255 may output the score directly to the subject of the test, to a trainer, a medical specialist, a vision specialist, other individual, data base, storage device, etc.

Having thus described the invention, what is claimed is:

1. A method for testing or training the contrast sensitivity of a subject, the method comprising:
   providing a display device viewable by the subject;
   providing an input device accessible to the subject capable of receiving, at a given time, at least one of any of a plurality of spatially defined inputs;
   displaying, on the display device, a plurality of circular contrast zones beginning at a first time, each of the plurality of circular contrast zones having the same total pigmentation, the plurality of circular contrast zones spatially arranged in correspondence with the plurality of spatially defined inputs capable of being received by the input device, and one of the plurality of circular zones having a higher contrast value than the other contrast zones, the one of the plurality of contrast zones having a higher contrast having a non-zero contrast value and the other circular contrast zones having a zero contrast value;
   receiving, at a second time an input from the subject at the input device, the input selecting one of the plurality of circular contrast zones;
   determining whether the circular contrast zone selected by the received input corresponds to the contrast zone having a higher contrast than the other contrast zones; and
   storing the determination as to whether the received spatially defined input corresponds to the contrast zone having a different contrast than the other contrast zones.

2. The method for testing or training the contrast sensitivity of a subject of claim 1, wherein the one of the circular contrast zones having a higher contrast than the other contrast zones displayed in the displaying step comprises a circular contrast zone having a sinusoidally varying total pigmentation along the diameter of the circular contrast zone.

3. The method for testing or training the contrast sensitivity of a subject of claim 1, wherein the one of the circular contrast zones having a higher contrast than the other contrast zones displayed in the displaying step comprises a circular contrast zone having a square wave varying total pigmentation along the diameter of the circular contrast zone.

4. The method for testing or training the contrast sensitivity of a subject of claim 1, wherein the one of the circular contrast zones having a higher contrast than the other contrast zones displayed in the displaying step comprises a circular contrast zone having a single portion that differs in total pigmentation from the rest of that circular contrast zone.

5. The method for testing or training the contrast sensitivity of a subject of claim 1, wherein the one of the circular contrast zones having a higher contrast than the other contrast zones displayed in the displaying step comprises a circular contrast zone having a non-periodic variance in total pigmentation.

6. A system for testing or training the contrast sensitivity of a subject, the system comprising:
   a display device that displays a plurality of spatially arranged circular contrast zones for viewing by the subject;
   an input device that receives any of a plurality of inputs from a subject, each of the plurality of inputs having a spatial relationship with the other plurality of inputs; and
   a test unit operably connected to the display device and to the input device;
   wherein:
   the test unit causes the display device to display at a first time a first plurality of circular contrast zones each having the same total pigmentation, the plurality of circular zones spatially arranged in correspondence with at least a subset of the plurality of inputs that the input device can receive, one of the first plurality of circular contrast zones having a higher contrast than the other contrast zones of the first plurality of contrast zones, the one of the plurality of contrast zones having a higher contrast having a non-zero contrast value and the other circular contrast zones having a zero contrast value;
   the test unit receives one of the plurality of inputs from the input device after a first time delay from the first time; and
   the test unit determines whether the received input corresponds to the one of the first plurality of circular contrast zones having a different contrast than the other contrast zones of the first plurality of contrast zones.

7. The system for testing or training the contrast sensitivity of a subject of claim 6, wherein the input device that receives any of a plurality of inputs from a subject, each of the plurality of inputs having a spatial relationship with the other plurality of inputs, comprises a multi-touch device that registers a directional touch.

8. The system for testing or training the contrast sensitivity of a subject of claim 7, wherein the first plurality of circular contrast zones spatially arranged in correspondence with at least a subset of the plurality of inputs the input device receives comprises displaying at least a top circular contrast zone, a bottom circular contrast zone, a left circular contrast zone, and a right circular contrast zone.

9. The system for testing or training the contrast sensitivity of a subject of claim 8, wherein any one of the top circular contrast zone, the bottom circular contrast zone, the left circular contrast zone, and the right circular contrast zone possesses a higher contrast pattern than the other circular contrast zones in the first plurality of contrast zones.

10. The system for testing the contrast sensitivity of a subject of claim 8, wherein the subject registers a response selecting one of the first plurality of circular contrast zones by touching the multi-touch device in a direction corresponding to one of the first plurality of circular contrast zones.

11. A method for performing a contrast sensitivity test on a subject, the method comprising:
   (a) providing a display device viewable to the subject;
   (b) providing an input device accessible to the subject;
   (c) displaying, on the display device, a plurality of circular contrast zones, each of the plurality of circular contrast zones having the same total pigmentation, one of the plurality of circular contrast zones having a higher contrast pattern than the other circular contrast zones of the plurality of contrast zones, the one of the plurality of contrast zones having a higher contrast pattern having a non-zero contrast value and the other circular contrast zones having a zero contrast value;
   (d) receiving, at the input device, an input from the subject, the input being in response to displaying the plurality of circular contrast zones, the input designating which of the plurality of circular contrast zones the subject perceives to have a higher contrast pattern than the other circular contrast zones of the plurality of contrast zones;
   (e) in response to receiving the input, ceasing to display the plurality of circular contrast zones;
   (f) determining whether the input correctly identified the circular contrast zone having the higher contrast pattern than the other circular contrast zones of the plurality of circular contrast zones; and
   (g) iteratively repeating steps (c)-(f) until the contrast sensitivity test has concluded.

12. The method of step 11, wherein the step of (b) providing an input device accessible to the subject comprises providing an input device accessible to the subject comprises providing a touch sensitive screen, and wherein the step of (d) receiving, at the input device, an input from the subject comprises detecting a touch of the touch sensitive screen.

13. The method of step 11, wherein the step of (g) iteratively repeating steps (c)-(f) until the contrast sensitivity test has concluded comprises iteratively repeating steps (d)-(f) a predetermined number of times, while changing the contrast of the one of the plurality of contrast zones having a higher contrast pattern than the other circular contrast zone each time step (c) of displaying, on the display device, a plurality of circular contrast zones is performed.

14. The method of step 11, wherein the step of (g) iteratively repeating steps (c)-(f) until the contrast sensitivity test has concluded comprises decreasing the difference in contrast between the one of the plurality of circular contrast zones having a higher contrast pattern than the other circular contrast zones each time step (c) of displaying, on the display device, a plurality of circular contrast zones until step (f) of determining whether the input correctly identified the circular contrast zone having the higher contrast pattern determines that the input incorrectly identified the circular contrast zone having the higher contrast pattern.

* * * * *